United States Patent
Nandi et al.

(10) Patent No.: US 11,013,702 B2
(45) Date of Patent: May 25, 2021

(54) MIDODRINE HYDROCHLORIDE ORAL SOLUTION AND USES THEREOF

(71) Applicant: Vertice Pharma, LLC, New Providence, NJ (US)

(72) Inventors: Indranil Nandi, Bridgewater, NJ (US); Ketan Hippalgaonkar, Mount Laurel, NJ (US); Sunil Vandse, Basking Ridge, NJ (US); Rish J. Vachhani, Parisppany, NJ (US)

(73) Assignee: Vertice Pharma, LLC, New Providence, NJ (US)

( * ) Notice: Subject to any disclaimer, the term of this patent is extended or adjusted under 35 U.S.C. 154(b) by 75 days.

(21) Appl. No.: 16/469,101

(22) PCT Filed: Oct. 10, 2018

(86) PCT No.: PCT/US2018/055300
§ 371 (c)(1),
(2) Date: Jun. 12, 2019

(87) PCT Pub. No.: WO2019/075127
PCT Pub. Date: Apr. 18, 2019

(65) Prior Publication Data
US 2020/0113851 A1    Apr. 16, 2020

Related U.S. Application Data

(60) Provisional application No. 62/570,470, filed on Oct. 10, 2017.

(51) Int. Cl.
*A61K 31/165* (2006.01)
*A61K 9/00* (2006.01)
*A61K 47/26* (2006.01)

(52) U.S. Cl.
CPC .......... *A61K 31/165* (2013.01); *A61K 9/0053* (2013.01); *A61K 47/26* (2013.01)

(58) Field of Classification Search
CPC ..... A61K 31/165; A61K 9/0053; A61K 47/26
See application file for complete search history.

(56) References Cited

U.S. PATENT DOCUMENTS

| | | | |
|---|---|---|---|
| 6,576,677 B1 * | 6/2003 | Ukai | A61K 9/0095 |
| | | | 514/772.4 |
| 8,715,730 B2 | 5/2014 | Takaki et al. | |
| 9,016,221 B2 | 4/2015 | Brennan et al. | |
| 2002/0034544 A1 | 3/2002 | Skinhoj et al. | |
| 2002/0147232 A1 | 10/2002 | Sundgreen et al. | |
| 2005/0281772 A1 | 12/2005 | Bromley et al. | |
| 2008/0312331 A1 | 12/2008 | Solomon | |
| 2016/0113867 A1 | 4/2016 | Cohen et al. | |
| 2016/0213665 A1 * | 7/2016 | Okamoto | A61P 25/00 |

FOREIGN PATENT DOCUMENTS

WO    WO 01/74334 A1    10/2001

OTHER PUBLICATIONS

Product Monograph, Midodrine hydrochloride Tablets 2.5 mg and 5 mg AAPharma Inc. Vaughan, Ontario, from AAPharma website: https://www.aapharma.ca/downloads/en/PIL/Midodrine_PM.pdf, Jul. 2010, Exhibit 10.

M.G. Quaglia, et al., Chiral investigation of midodrine, a long-acting alpha-adrenergic stimulating agent. Chirality. Jul. 2004;16(6):356-62, Exhibit 11.

H.K. Jain, et al., Stability indicating RP-HPLC assay method for estimation of midodrine hydrochloride in bulk and tablets. International Journal of Pharmacy and Pharmaceutical Sciences. Sep. 2016; 8(9):283, Exhibit 12.

* cited by examiner

*Primary Examiner* — Genevieve S Alley
(74) *Attorney, Agent, or Firm* — Adriano & Associates

(57) ABSTRACT

The invention provides oral liquid midodrine formulation and uses thereof.

16 Claims, 3 Drawing Sheets

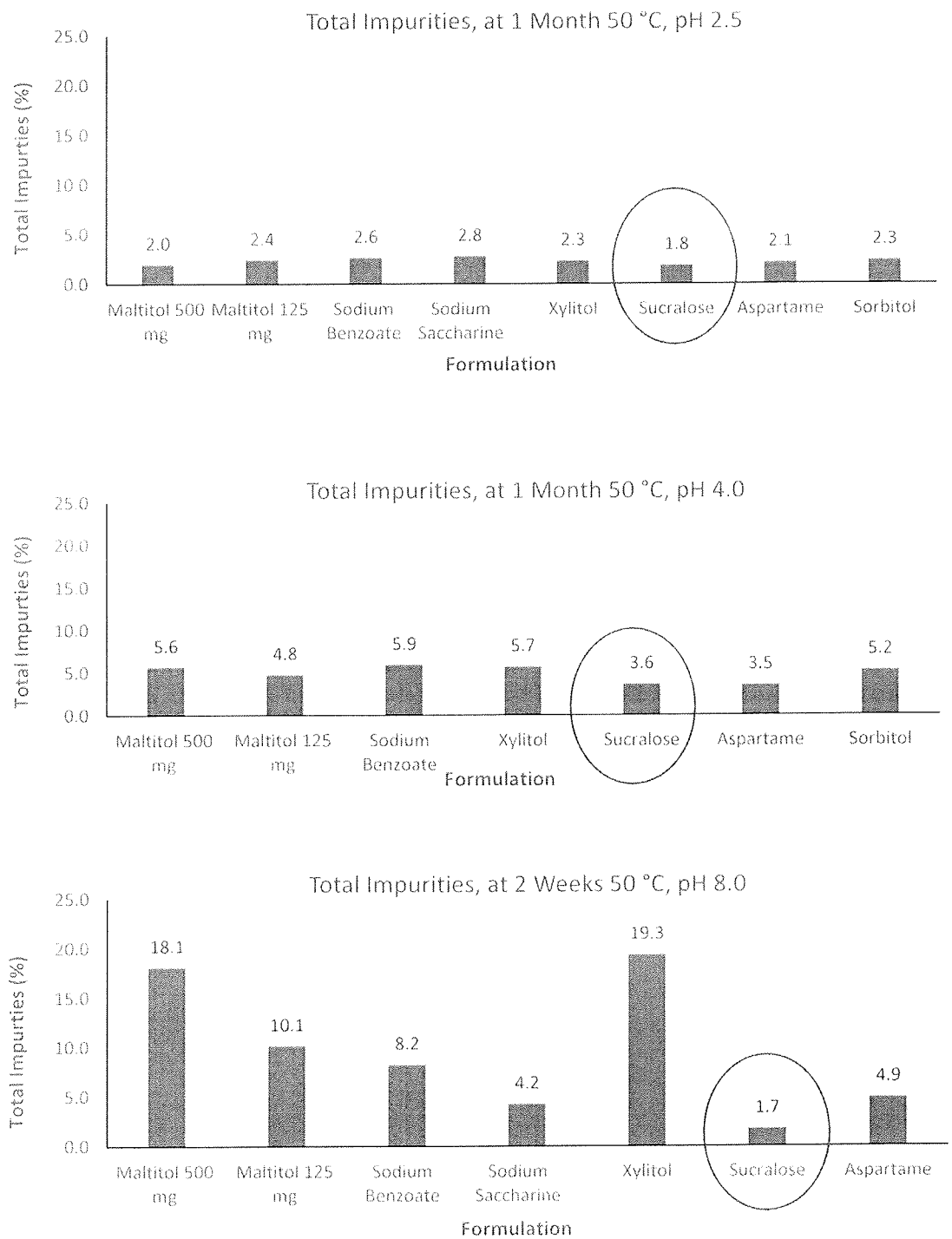
Figure 1 : Total Impurities as a Function of Formulations at Different pH Values

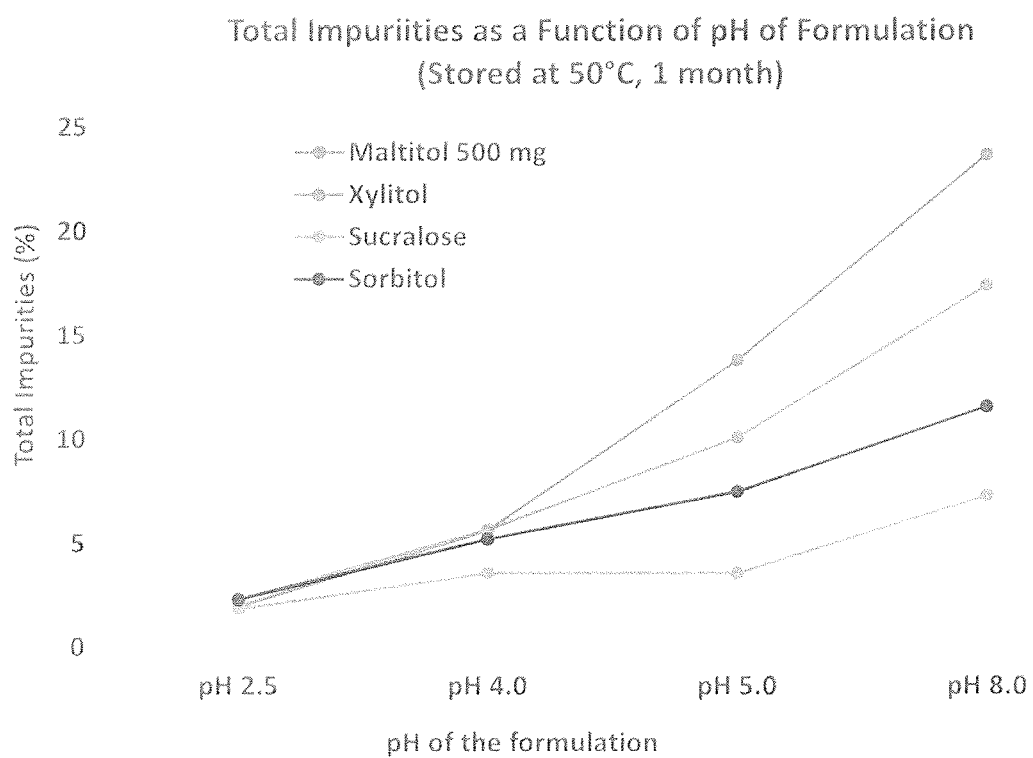
Figure 2: Total Impurities as a Function of pH of formulation

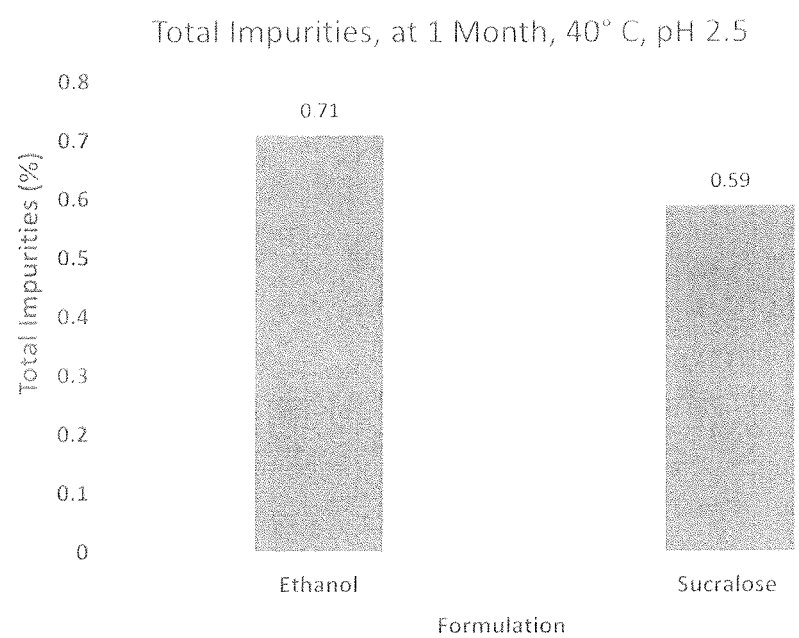
Figure 3: Total Impurities of Ethanol and Sucralose Formulations at End of One month's Storage at 40 °C at pH 2.5

MIDODRINE HYDROCHLORIDE ORAL SOLUTION AND USES THEREOF

CROSS REFERENCE TO RELATED APPLICATIONS

The subject application claims priority under 35 U.S.C. 371 to PCT Application No. PCT/US2018/055300, filed Oct. 10, 2018, which claims the benefit to U.S. Provisional Application No. 62/570,470, filed Oct. 10, 2017, all of which are incorporated herein by reference in their entireties into the present patent application for all purposes.

Throughout this application various publications are referenced. The disclosures of these publications in their entireties are hereby incorporated by reference into this application in order to more fully describe the state of the art to which this invention pertains.

BACKGROUND OF THE INVENTION

Orthostatic or postural hypotension is defined as a sustained reduction in systolic blood pressure (BP) of at least 20 mmHg or a reduction in diastolic BP of at least 10 mmHg within three minutes of standing or head-up tilt to an angle of at least 60° [1,2]. The inability to maintain blood pressure (BP) in the standing position, can lead to lightheadedness, weakness, dizziness, difficulty in concentrating, palpitation, anxiety, near syncope and syncope[3].

The reported prevalence of orthostatic hypotension (OH) is age dependent, ranging from 5% in patients <50 years of age to 30% in those >70 years of age[3]. In elderly patients, OH can significantly affect morbidity, cause disability as a result of falls and fractures, and increase the risk of overall mortality.

OH occurs predominantly by delayed constriction of the lower body blood vessels, which is normally required to maintain an adequate blood pressure when changing position to standing. Thus, blood pools in the blood vessels of the legs for a longer period, and less is returned to the heart, thereby leading to a reduced cardiac output. Mild orthostatic hypotension is common and can occur briefly in anyone, although it is prevalent among the elderly, and those with known low blood pressure. Severe drops in blood pressure can lead to fainting with a possibility of injury. There are numerous possible causes for OH, such as certain medications (e.g. alpha blockers), autonomic neuropathy, decreased blood volume, and age-related blood vessel stiffness.

OH is caused primarily by gravity-induced blood-pooling in the lower extremities, which in turn compromises venous return, resulting in decreased cardiac output and subsequent lowering of arterial pressure. For example, changing from a lying position to standing loses about 700 ml of blood from the thorax, with a decrease in systolic and diastolic blood pressures. The overall effect is an insufficient blood perfusion in the upper part of the body. Still, the blood pressure does not normally fall very much, because it immediately triggers a vasoconstriction (baroreceptor reflex), pressing the blood up into the body again. (Often, this mechanism is exaggerated and is why diastolic blood pressure is bit higher when a person is standing up, compared to a person in horizontal position). Therefore, a secondary factor that causes a greater than normal fall in blood pressure is often required. Such factors include low blood volume, diseases, and medications.

Currently, midodrine hydrochloride has an orphan designation status and marked as oral tablets at strengths of 2.5, 5 and 10 mg. However, the convenience and compliance is an issue for geriatric patients. Hence, the discovery herein is an oral solution to enable these patients to administer the drug conveniently.

Oral Tablets: Shire produced branded drug product in oral tablet dosage form (ProAmatine®) and the generic versions of the same are manufactured by Apotex, Impax Laboratories, Mylan Pharmaceuticals, Sandoz and Upsher-Smith. The tablets are available in 2.5 mg, 5 mg, and 10 mg strengths.

Oral Drop: The oral solution Gutron® Oral drop was developed for Austrian market. However, there are no approved oral solution dosage form of midodrine in the United States.

A need remains for an oral midodrine hydrochloride solution that is stable and safe and made available to the patient population. This discovery addresses that need.

SUMMARY OF THE INVENTION

The invention provides an oral liquid formulation of midodrine or a pharmaceutically acceptable salt thereof stabilized by a sweetener comprising: midodrine or a pharmaceutically acceptable salt of midodrine and a sweetener and methods for treatment using such liquid formulations.

The invention further provides a stable, oral liquid formulation of midodrine hydrochloride (midodrine HCL) comprising: midodrine HCL and sucralose. In a further embodiment, pH of the formulation may be from pH 3 to 7. In a further embodiment, the formulation further comprises methylparaben and propylparaben.

The invention additionally provides a stable, oral liquid formulation of midodrine HCL comprising: midodrine HCL and an artificial or non-nutritive sweetener which serves a dual function, namely as a sweetener and a stabilizing agent of midodrine. In an embodiment, the formulation comprises sucralose. In a separate embodiment, the formulation comprises aspartame. In a further embodiment, pH of the formulation may be from pH 3 to 7. In a further embodiment, the formulation further comprises methylparaben and propylparaben.

The invention also provides a stable, oral liquid formulation of midodrine HCL comprising midodrine HCL and a sucralose, wherein no more than 10% by weight of the degradation product of midodrine HCL may be present at commercially relevant stability conditions including, e.g., being stored for about 3-6 months at 40 degrees Centigrade or at least about 2 years at 25° C.

Additionally, the invention provides a stable, oral liquid formulation of midodrine HCL comprising midodrine HCL and a sucralose, wherein no more than about 1.1% by weight of the degradation product of midodrine HCL may be present for pH 3.5 formulation after storage at 25 degrees Centigrade and 60% relative humidity for 6 months.

BRIEF DESCRIPTION OF DRAWINGS

FIG. 1. Bar graph showing total impurities as a function of formulations at different pH values. Irrespective of pH of the formulation, total impurities are observed to be lower for the sucralose formulation. Formulation containing sucralose showed best stability of the drug irrespective of the pH of the formulation.

FIG. 2. Line graph showing total impurities as a function of pH of the formulations. Stability of midodrine HCL is highly dependent on pH of the formulation. As pH value of the formulation increases, increases in total impurity levels are observed. Irrespective of pH of the formulation, total impurities are observed to be lower for the sucralose formulation.

FIG. 3. Bar graph showing total impurities in ethanol and sucralose formulation at end of one month storage at 40 degrees Centigrade at pH 2.5.

LIST OF TABLES

Table 1. Test midodrine oral liquid formulations.
Table 2. Gradient HPLC analysis program for midodrine oral solution.
Table 3. Solubility of midodrine hydrochloride in various solvents and pH Values.
Table 4. Percent total impurities for formulations at 1 month, 50° C. as a function of pH.
Table 5. Percent total impurities for formulations at 3 months, 40° C.±2° C./75%±5% RH as a function of pH.
Table 6. Percent total impurities for formulations at 3 months, 25° C.±2° C./60%±5% RH as a function of pH.
Table 7. Effect of sucralose on total impurities as a function of formulation pH at various stability condition.
Table 8. Percent decrease or inhibition of midodrine degradation at different pH values by sucralose (compared to same formulation at the same pH but without sucralose).
Table 9. Stability results for midodrine hydrochloride oral solution, 2.5 mg/5 mL, pH 3.5.
Table 10. Formulation composition of midodrine hydrochloride oral solution, 2.5 mg/5 mL, pH 3.5 used in Table 9.
Table 11. Total impurities of formulation with or without sucralose at pH 3.5.
Table 12: Percent decrease or inhibition of midodrine degradation by sucralose at pH 3.5 (compared to same formulation at pH 3.5 but without sucralose).
Table 13. Exemplary midodrine oral liquid formulation.
Table 14. Alternative midodrine oral liquid formulations stabilized by sucralose.

DETAILED DESCRIPTION OF THE INVENTION

All scientific and technical terms used in this application have meanings commonly used in the art unless otherwise specified. As used in this application, the following words or phrases have the meanings specified.

Midodrine Hydrochloride (HCL) has the chemical name, 2-amino-N-[2-(2,5-dimethoxyphenyl) -2-hydroxyethyl]acetamide hydrochloride. It is also referred to as 2-amino-N-(β-hydroxy-2,5-dimethoxy-phenethyl)-acetamide hydrochloride. Its relative molecular mass is about 290.74. It has the following molecular formula: $C_{12}H_{19}ClN_2O_4$ with a CAS No. 3092-17-9. Its structural formula is as follows:

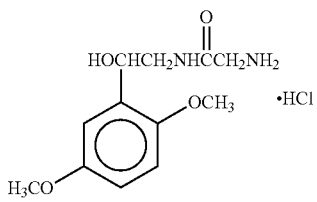

A "solution" is a liquid dosage form. Merely by way of example, each 10 mL of a midodrine HCL solution may contain 5 mg±10% of midodrine HCL.

The term "effective amount" means an amount of a compound/composition according to the present invention effective in producing the desired therapeutic effect.

The term "about" means +/−10% of the stipulated value unless indicated otherwise.

The term "treating" a disease or condition, means to manage a disease or condition with the pharmaceutical formulation of the invention. Treatment can decrease the symptoms of a disease or condition, reduce the severity of a disease or condition, alter the course of disease progression or condition, ameliorate and/or cure a disease or condition. The disease or condition may include but not limited to orthostatic hypotension, syncope, orthostatic intolerance, symptomatic hypotension (e.g. hypotension associated with infections, the convalescent period, surgical operations, delivery, or changes in the weather as well as what is called "difficulties in getting started in the mornings"), urinary incontinence, septic shock and conditions responsive to alpha-1 adrenergic (A1) receptor stimulation.

As used herein, the term "active agent" refers to active pharmaceutical ingredient (API), including a prodrug.

As used herein, the term "stable" in the context of a liquid formulation of the invention refers to the resistance of midodrine to thermal and chemical degradation under given manufacture, preparation, transportation and storage conditions. The "stable" formulations of the invention may retain activity equal to or more than about 90%, 95%, 98%, 99% or 99.5% of midodrine activity under given manufacture, preparation, transportation and storage conditions for at least five months, for six months or more. Stability can be measured using any physicochemical characterization techniques known to those skilled in the art, such as, for example high pressure liquid chromatography (HPLC). Preferably the compositions have sufficient stability to allow storage at a commercially relevant temperature, such as between about 0° Centigrade (C) and about 60° C., for a commercially relevant period of time, such as at least one week, preferably at least one month, more preferably at least three months, and most preferably at least six months. The commercially relevant temperature may be an elevated temperature between 40° C. and 60° C. to subject the composition to a stress test condition to expedite formation of degradation or decomposition products, or alternatively, may be retail or consumer relevant temperature between 4° C. and 25° C., a temperature typically associated with a shelf life of a drug product. In some embodiments, the shelf life of a drug product may be determined not only on measured stability of the composition stored at a defined temperature but also may be based on the date of product use by the consumer. In some embodiments, the compositions have sufficient stability to allow storage at a commercially relevant temperature for more than one year, and in some embodiments more than two years.

A degradation product may be an impurity resulting from a chemical change in the drug substance brought about during manufacture, transportation and/or storage of the new drug product by the effect of, for example, light, temperature, pH, water, or by reaction with an excipient and/or the immediate container closure system.

COMPOSITIONS OF THE INVENTION

The invention provides stable oral liquid formulations of midodrine or a pharmaceutically acceptable salt thereof, stabilized by a sweetener comprising: midodrine or a pharmaceutically acceptable salt of midodrine and a sweetener. In accordance with the practice of the invention, the liquid formulation may be a solution. In further embodiments, the solution may be in the form of an aqueous solution. Suitable examples of inorganic acids include, but are not limited to, a hydrochloric acid, a hydrobromic acid, a hydroiodic acid, a nitric acid, a nitrous acid, a phosphorous acid, a phosphoric acid, a sulfuric acid and a peroxysulfuric acid and a combination thereof. In accordance with the practice of the invention, the liquid formulation may also be a solution, a mixture, or syrup.

The invention provides an aqueous formulation comprising midodrine or a pharmaceutically acceptable salt thereof as only active agent added to the formulation, sucralose as a sweetener and stabilizing agent of midodrine, methylparaben and propylparaben as preservatives and purified water as a carrier. The invention further provides an aqueous formulation comprising midodrine or a pharmaceutically acceptable salt thereof as only active agent added to the formulation, sucralose as a sweetener and stabilizing agent of midodrine, methylparaben and propylparaben as preservatives, orange vanilla flavor as a flavor and water as a carrier. Additionally, the invention also provides an aqueous formulation consisting of midodrine, sucralose, methylparaben, propylparaben, orange vanilla flavor, HCl/NaOH and purified water.

In accordance with the practice of the invention, midodrine may be present in the form of (±)-2-amino-N-(β-hydroxy-2,5-dimethoxyphenethyl)acetamide, (±)-2-amino-N-(β-hydroxy-2,5-dimethoxyphenethyl)acetamide, or (−)-2-amino-N(β-hydroxy-2,5-dimethoxyphenethyl)acetamide or mixtures thereof.

In a preferred embodiment, the midodrine may be present in the form of a pharmaceutically acceptable salt, midodrine hydrochloride (midodrine HCL). In another embodiment, the active agent in the formulation may be midodrine HCL. In a preferred embodiment, midodrine is present in the racemic mixture form (RS). In a preferred embodiment, midodrine may be a hydrochloride salt of a racemic mixture, (±)-2-amino-N-(β-hydroxy-2,5-dimethoxyphenethyl)acetamide. In a more preferred embodiment, midodrine may be a hydrochloride salt of enriched for the enantiomeric form, (−)-2-amino-N(β-hydroxy-2,5-dimethoxyphenethyl)acetamide. In yet a further embodiment, midodrine may be the only active agent or active pharmaceutical ingredient in the formulation or used in producing a pharmaceutical composition of the formulation. In one embodiment of the invention, the midodrine or its pharmaceutically acceptable salt may be the only active agent or active pharmaceutical ingredient added to the formulation. In an embodiment, midodrine, a prodrug, may be metabolized after administration to a subject into a pharmacologically active drug, desglymidodrine—an alpha-1 adrenergic (A1) receptor agonist.

Suitable sweeteners are sweeteners which not only function as a sweetener but also function to stabilize midodrine in aqueous formulation during storage, and hence serve additionally as a stabilizing agent of midodrine to inhibit or prevent its degradation over a range of pH. Applicants have found that sweeteners as excipients may promote degradation of aqueous solution of midodrine. In particular, Applicants found sugar alcohols, polyols (e.g., maltitol and sorbitol), to destabilize midodrine, promoting formation of midodrine degradation products, especially under super accelerated (50° C. at ambient humidity) or accelerated (40° C.±2° C./75%±5% RH) storage conditions. In contrast, Applicants find that artificial sweeteners, such as sucralose and aspartame, can stabilize oral liquid formulation comprising midodrine, inhibiting or preventing degradation of midodrine. Merely by way of example, in one embodiment, the formulation may have a shelf life of at least about 3 months, 6 months, 1 year or 2 years. In another embodiment, the formulation has a shelf life of at least about 2 years. As such, in one embodiment, sucralose may serve not only as a sweetener but also as a stabilizing agent of midodrine, extending shelf life of an oral liquid formulation comprising midodrine or midodrine-HCl.

In one embodiment of the invention, the formulation may further comprise a paraben. Examples of the paraben may include, but are not limited to, methylparaben, ethylparaben, propylparaben and butylparaben. Examples of the paraben may also include, but are not limited to, methylparaben, propylparaben and a combination thereof. In another embodiment of the invention, the formulation further comprises a methylparaben and a propylparaben. Stabilization of midodrine by sucralfate may be observed in a formulation additionally comprising methylparaben and propylparaben as preservatives from pH 3.0 to 8.0. In another embodiment, aspartame may serve not only as a sweetener but also as a stabilizing agent of midodrine, extending shelf life of an oral liquid formulation comprising midodrine or midodrine-HCl. Stabilization of midodrine by aspartame may be observed in a formulation additionally comprising methylparaben and propylparaben as preservatives from pH 4.0 to 5.0 and may extend to pH 8.0. It would be clear to one skilled in the art that preservatives may be substances added to protect the product from microbiological growth or inhibit the growth of microorganisms.

A stabilizing agent of midodrine may inhibit or prevent its degradation over a range of pH. It may also prevent or inhibit the breakdown of midodrine or its transformation to a midodrine adduct.

Merely by way of example, in one embodiment, the pH of the formulation maybe at least pH 3 or greater. In another embodiment, the pH of the formulation maybe at least pH 3.5 or greater. In yet a further embodiments, the pH of the formulation maybe at least pH 4.0 or greater; the pH of the formulation may be least pH 4.5 or greater; the pH of the formulation maybe at least pH 5.0 or greater; In yet another embodiment, pH of the formulation maybe at least pH 5.5 or greater; the pH of the formulation maybe at least pH 6.0 or greater; the pH of the formulation maybe at least pH 6.5 or greater; the pH of the formulation maybe pH 8.0 or lower; the pH of the formulation maybe pH 7.5 or lower; the pH of the formulation maybe pH 7.0 or lower; the pH of the formulation maybe between pH 3.0 and 7.0; the pH of the formulation maybe between pH 3.5 and 6.5; the pH of the formulation maybe between pH 4.0 and 6.0.

Examples of the pH of the formulation include, but are not limited to, any of 3.0±0.1, 3.1±0.1, 3.2±0.1, 3.3±0.1, 3.4±0.1, 3.5±0.1, 3.6±0.1, 3.7±0.1, 3.8±0.1, 3.9±0.1, 4.0±0.1, 4.1±0.1, 4.2±0.1, 4.3±0.1, 4.4±0.1, 4.5±0.1, 4.6±0.1, 4.7±0.1, 4.8±0.1, 4.9±0.1, 5.0±0.1, 5.1±0.1, 5.2±0.1, 5.3±0.1, 5.4±0.1, 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, and 7.0±0.1.

Merely by way of example, in one specific embodiment, pH of the formulation maybe 3.0±0.1. In other specific embodiments, the pH of the formulation maybe 3.5±0.1; the pH of the formulation maybe 4.0±0.1; the pH of the formulation maybe 4.5±0.1; or the pH of the formulation is 5.0±0.1.

In one embodiment of the invention, the pH of the formulation may change during storage. For example, in one embodiment, the change in during storage maybe toward pH 6 or 7. In another embodiment, the change in pH during storage maybe toward pH 5.6±0.2.

In another specific embodiment of the invention, the pH of the formulation maybe 3.5±0.1 and sucralose may either reduce or at least does not promote degradation of midodrine.

In one embodiment, no more than about 3.0% by weight of the degradation product of midodrine is present after being stored for 1 month at 50 degrees Centigrade and ambient humidity for a formulation with an initial pH of 3.5. In a further embodiment, the sucralose inhibits midodrine degradation by about 0.6% or at least 0.4% of total midodrine used in the formulation.

In a specific embodiment, no more than about 2.9% by weight of the degradation product of midodrine is present after being stored for 3 months at 40 degrees Centigrade and relative humidity of 75% for a formulation with an initial pH of 3.5. In a further embodiment, the sucralose may inhibit midodrine degradation by about 0.2% or at least 0.1% of total midodrine used in the formulation.

Further, in one embodiment, no more than about 0.9% by weight of the degradation product of midodrine is present after being stored for 3 months at 30 degrees Centigrade and relative humidity of 65% for a formulation with an initial pH of 3.5. In an additional embodiment, the sucralose inhibits midodrine degradation by about 0.1% of total midodrine used in the formulation.

In yet another embodiment, no more than about 0.5% by weight of the degradation product of midodrine is present after being stored for 3 months at 25 degrees Centigrade and relative humidity of 60% for a formulation with an initial pH of 3.5. In a further embodiment, the sucralose inhibits midodrine degradation by about 0.2% or at least 0.1% of total midodrine used in the formulation.

Additionally, in an embodiment of the invention, no more than about 6.5% by weight of the degradation product of midodrine is present after being stored for 6 months at 40 degrees Centigrade and relative humidity of 75% for a formulation with an initial pH of 3.5. In another embodiment, no more than about. 1.8% by weight of the degradation product of midodrine is present after being stored for 6 months at 30 degrees Centigrade and relative humidity of 65% for a formulation with an initial pH of 3.5. In yet another embodiment, no more than about 1.1% by weight of the degradation product of midodrine is present after being stored for 6 months at 25 degrees Centigrade and relative humidity of 60% for a formulation with an initial pH of 3.5.

Suitable sweeteners of the invention include any sweetener that not only serves to increase sweetness or improve palatability but also as a stabilizing agent of midodrine so as to inhibit or prevent midodrine degradation. In an embodiment, suitable sweeteners include, but are not limited to, artificial or non-nutritive sweeteners. In another embodiment, suitable sweeteners include any sweetener that not only serves to increase sweetness or improve palatability but also as a stabilizing agent of midodrine in a formulation comprising methylparaben and propylparaben. In an embodiment, suitable sweeteners include, but are not limited to, artificial or non-nutritive sweeteners. In a separate embodiment, suitable sweeteners include any sweetener that not only serves to increase sweetness or improve palatability but also as a stabilizing agent of midodrine in a formulation over a range of pH from 3.0 to 8.0, pH 3.0 to 7.0 or pH 3.5 to 7.0. In an embodiment, suitable sweeteners include, but are not limited to, artificial or non-nutritive sweeteners. In another embodiment, suitable sweeteners include any sweetener that not only serves to increase sweetness or improve palatability but also as a stabilizing agent of midodrine in a formulation comprising methylparaben and propylparaben and over a range of pH from 3.0 to 8.0, pH 3.0 to 7.0 or pH 3.5 to 7.0. In an embodiment, suitable sweeteners include, but are not limited to, artificial or non-nutritive sweeteners.

In one embodiment of the invention, sucralose decreases degradation of midodrine HCL over a range of pH from 4.0 to 8.0 compared to the same formulation without sucralose. In a further embodiment, sucralose is more effective at decreasing degradation of midodrine HCL than maltitol, xylitol or sorbitol over a range of pH from 4.0 to 5.0.

In one embodiment, sucralose stabilizes the formulation over a range of pH from 3.0 to 8.0 than the same formulation without sucralose.

Suitable artificial or non-nutritive sweeteners include, but are not limited to, sucralose, aspartame, acesulfame potassium (Ace-K0), neotame, advantame, steviol glycoside, and Luo Han Guo fruit extract and/or a pharmaceutically acceptable salt thereof and combination thereof. In a preferred embodiment, the artificial or non-nutritive sweetener is aspartame and/or a pharmaceutically acceptable salt thereof. In a more preferred embodiment, the artificial or non-nutritive sweetener is sucralose and/or a pharmaceutically acceptable salt thereof.

In an embodiment, suitable sweeteners may be natural sweetener so long as the sweetener does not destabilize midodrine leading to acceleration in the production of midodrine breakdown products. Suitable natural sweeteners include, but are not limited to, hydrogenated glucose syrup, hydrogenated starch hydrolysate, isomalt, molasses, molasses extract, agave syrup, orange syrup, raspberry syrup, concentrated raspberry juice, concentrated peppermint emulsion, anise water, concentrated camphor water, liquorice liquid extract, vanilla extract and orange-vanilla extract. In one embodiment of the invention, the formulation further comprises a flavor. Examples of the flavor include, but are not limited to, molasses, molasses extract, agave syrup, orange syrup, raspberry syrup, concentrated raspberry juice, concentrated peppermint emulsion, anise water, concentrated camphor water, liquorice liquid extract, vanilla extract, orange extract and orange-vanilla extract. In one embodiment, the flavor does not promote degradation of midodrine. In one embodiment, the flavor is orange-vanilla extract. In one embodiment, a sweetener may also be a flavor, so long as the flavor does not promote midodrine degradation or promotes midodrine degradation to any appreciable extent which cannot be reversed by inclusion of a $2^{nd}$ sweetener in the formulation, wherein the $2^{nd}$ sweetener further stabilizes midodrine. Examples of flavor include but are not restricted to molasses, molasses extract, agave syrup, orange syrup, raspberry syrup, concentrated raspberry juice, concentrated peppermint emulsion, anise water, concentrated camphor water, liquorice liquid extract, vanilla extract, orange extract and orange-vanilla extract. In an embodiment, flavor may be used interchangeably with flavoring.

In a preferred embodiment, the sweetener is a sucralose. Merely by way of example, the sweetener may inhibit hydrolysis or degradation of midodrine, thereby resulting in the oral liquid formulation of midodrine or a pharmaceutically acceptable salt of midodrine stabilized by the sweetener. The hydrolysis of midodrine may be pH dependent. For example, hydrolysis of midodrine may increase with increasing pH.

The invention provides a stable oral liquid formulation of midodrine or a pharmaceutically acceptable salt thereof, stabilized by sucralose comprising: midodrine or a pharmaceutically acceptable salt of midodrine and sucralose.

In one embodiment of the invention, the formulation additionally comprises an artificial or non-nutritive sweetener. In a further embodiment, the artificial or non-nutritive sweetener does not promote formation of midodrine degradation products or inhibits formation of midodrine degradation products. Further, in an embodiment, the artificial or non-nutritive sweetener does not promote formation of midodrine degradation products or inhibits formation of midodrine degradation products from pH 3.0 to 8.0 In another embodiment, the artificial or non-nutritive sweetener does not promote formation of midodrine degradation products or inhibits formation of midodrine degradation products from pH 3.0 to 7.0 Examples of the pH may include, but are not limited to, about 3.0±0.1, 3.1±0.1, 3.2±0.1, 3.3±0.1, 3.4±0.1, 3.5±0.1, 3.6±0.1, 3.7±0.1, 3.8±0.1, 3.9±0.1, 4.0±0.1, 4.1±0.1, 4.2±0.1, 4.3±0.1, 4.4±0.1, 4.5±0.1, 4.6±0.1, 4.7±0.1, 4.8±0.1, 4.9±0.1, 5.0±0.1, 5.1±0.1, 5.2±0.1, 5.3±0.1, 5.4±0.1, 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, and 7.0±0.1.

In an embodiment, the formulation additionally comprises two or more sweeteners. In one embodiment, the formulation comprises a sweetener which stabilizes midodrine in aqueous solution. In one embodiment, the formulation comprises two or more sweeteners which stabilize midodrine in aqueous solution. In one embodiment, the sweetener stabilizes midodrine by reducing its breakdown. In one embodiment, the sweetener stabilizes midodrine by reducing its breakdown over a range of pH. In one embodiment, the sweetener stabilizes midodrine by reducing its breakdown from pH 2.5 to 8.0. In one embodiment, the sweetener stabilizes midodrine by reducing its breakdown from pH 3.0 to 8.0. In one embodiment, the sweetener stabilizes midodrine by reducing its breakdown from pH 3.0 to 7.0. In one embodiment, the sweetener stabilizes midodrine by reducing its breakdown from pH 3.5 to 7.0. In one embodiment, the sweetener stabilizes midodrine by reducing its breakdown from pH 3.5 to 6.5.

In one embodiment, the sweetener stabilizes midodrine by reducing its breakdown from pH 3.5 to 5.5. In one embodiment, the sweetener stabilizes midodrine by reducing its breakdown at pH 3.5. In another embodiment, the sweetener stabilizes midodrine by reducing its breakdown at pH 4.0. In another embodiment, the sweetener stabilizes midodrine by reducing its breakdown at pH 5.0. In one embodiment, the formulation comprises midodrine, a sweetener and a flavor.

In one embodiment, sucralose decreases degradation of midodrine over a range of pH from 4.0 to 8.0 than the same formulation lacking sucralose. In a further embodiment, sucralose is more effective at decreasing degradation of midodrine than maltitol, xylitol or sorbitol over a range of pH from 4.0 to 5.0. In another embodiment, sucralose stabilizes the formulation over a range of pH from 4.0 to 8.0.

Additionally in an embodiment of the invention, the destabilizing effect of sucralose at pH 2.5 is less than the stabilizing effect of sucralose from pH 4.0 to 8.0 when stored for the same duration and under same storage condition. In another embodiment, the destabilizing effect of sucralose at pH 2.5 may comprise the formation of midodrine degradation products.

Merely by way of example, in one embodiment, the formulation may be stored for at least 2 weeks, 1 month, 3 months, 6 months, 1 year or 2 years without substantial degradation. In particular embodiments, the formulation maybe stored for at least 3 months; in another embodiment, the formulation maybe stored for at least 6 months; the formulation maybe stored for at least 12 months; or the formulation is stored for at least 2 years.

Further, in an additional examples, the formulation maybe stored at a temperature greater than 20° C.; the formulation maybe stored at a temperature less than 65° C.; the formulation maybe stored at a temperature between 20° C. and 65° C.; the formulation maybe stored at a temperature between 25° C. and 50° C.; or the formulation maybe stored at a temperature of about 25° C. 30° C., 40° C. or 50° C.

Also, in particular embodiments, the formulation maybe stored at ambient humidity; the formulation maybe stored at relative humidity between about 55% and 80%; or the formulation maybe stored at a relative humidity of 60%±5%, 65%±5% or 75%±5%.

In a specific embodiment, the formulation is stored at 25° C.±2° C. and relative humidity of 60%±5%. In another embodiment, the formulation maybe stored at 30° C.±2° C. and relative humidity of 65%±5%. In yet another embodiment, the formulation maybe stored at 40° C.±2° C. and relative humidity of 75%±5%. In yet a further embodiment, the formulation maybe stored at 50° C.±2° C. and ambient humidity.

In an embodiment, the formulation additionally comprises a flavor. In another embodiment, the formulation additionally comprises two or more flavors. In one embodiment, the formulation additionally comprises a sweetener which is also a flavor. In one embodiment, the formulation comprises two or more sweeteners in which at least one of the sweetener is also a flavor. In one embodiment, the formulation additionally comprises one or more flavors. In one embodiment, the formulation comprises midodrine, a sweetener and a flavor.

In accordance with the practice of the invention, in a preferred embodiment, midodrine is midodrine hydrochloride or midodrine HCL.

In accordance with the practice of the invention, the formulation is a solution, e.g., an aqueous solution. In additional embodiments, the liquid may be in the form of a syrup.

Additionally, the invention provides an aqueous formulation comprising midodrine as only active agent, a sweetener, a preservative, a flavor and a carrier. Moreover, the invention also provides an aqueous formulation consisting of midodrine as only active agent, a sweetener, a preservative, a flavor, a carrier and an acid and/or a base. In another embodiment, the formulation may have a shelf life of at least 3 months with no more than 10% degradation product of midodrine during storage.

The invention provides a stable, oral liquid formulation of midodrine hydrochloride (midodrine HCL) comprising: midodrine HCL and sucralose. In a further embodiment, the formulation further comprises a paraben. In a further embodiment, the formulation further comprises two or more parabens. In an embodiment, the formulation further comprises a methylparaben and a propylparaben. In a further embodiment, the formulation has a pH of 3.0 to 7.0. In a further embodiment, the formulation has a pH of 3.5. In a further embodiment, the formulation has a starting pH of 3.5 and over course of storage increases in pH.

In an embodiment, the stable, oral liquid formulation of midodrine or midodrine hydrochloride is free of cyclamate or sodium cyclamate. In an embodiment, the stable, oral liquid formulation of midodrine or midodrine hydrochloride is free or substantially free of alcohol or alkyl alcohol. In an embodiment, the alcohol or alkyl alcohol is ethanol. In further embodiment, the stable, oral liquid formulation of midodrine or midodrine hydrochloride is free of sodium cyclamate and ethanol.

The invention additionally provides a stable, oral liquid formulation of midodrine HCL comprising: midodrine HCL and an artificial sweetener which serves a dual function, namely as a sweetener and a stabilizing agent of midodrine or midodrine hydrochloride. In an embodiment, the formulation comprises sucralose. In a separate embodiment, the formulation comprises aspartame. In a further embodiment, pH of the formulation is from pH 3 to 7. In a further embodiment, the formulation further comprises methylparaben and propylparaben.

The invention further provides a stable, oral liquid formulation of midodrine comprising midodrine and a sucralose, wherein no more than about 10% by weight of the degradation product of midodrine HCL is present at commercially relevant stability conditions including, e.g., being stored for about 3-6 months at 40 degrees Centigrade or at least 2 years at 25° C.

The invention also provides a stable, oral liquid formulation of midodrine comprising midodrine HCL and sucralose, wherein no more than about 10% by weight of the degradation product of midodrine HCL is present after being stored for 1 month at 50 degrees Centigrade.

Additionally, the invention also provides a stable, oral liquid formulation of midodrine comprising midodrine and a sucralose, wherein no more than about 1.1% by weight of the degradation product of midodrine HCL is present at for pH 3.5 formulation after storage at 25 degrees Centigrade and 60% relative humidity for 6 months.

In one embodiment, the sucralose decreases or inhibits midodrine degradation by at least 10% at pH 4.0 after being stored for 1 month at 50 degrees Centigrade and ambient humidity when compared to the same midodrine solution stored under the same condition but without sucralose. In another embodiment of the invention, the sucralose decreases or inhibits midodrine degradation by at least 4% at pH 5.0 after being stored for 1 month at 50 degrees Centigrade and ambient humidity when compared to the same midodrine solution stored under the same condition but without sucralose. In another embodiment, the sucralose decreases or inhibits midodrine degradation by at least 30% at pH 8.0 after being stored for 1 month at 50 degrees Centigrade and ambient humidity when compared to the same midodrine solution stored under the same condition but without sucralose. In yet another embodiment, the sucralose decreases or inhibits midodrine degradation by at least 13% at pH 4.0 after being stored for 3 months at 40 degrees Centigrade and 75% relative humidity when compared to the same midodrine solution stored under the same condition but without sucralose. Additionally, the sucralose decreases or inhibits midodrine degradation by at least 10 percent at pH 5.0 after being stored for 3 months at 40 degrees Centigrade and 75% relative humidity when compared to the same midodrine solution stored under the same condition but without sucralose.

Yet in another embodiment of the invention, the sucralose decreases or inhibits midodrine degradation by at least 50 percent at pH 8.0 after being stored for 3 months at 40 degrees Centigrade and 75% relative humidity when compared to the same midodrine solution stored under the same condition but without sucralose. Still, in one embodiment of the invention, the sucralose decreases or inhibits midodrine degradation by at least 40 percent at pH 4.0 alter being stored for 3 months at 25 degrees Centigrade and 60% relative humidity when compared to the same midodrine solution stored under the same condition but without sucralose.

In another embodiment of the invention, the sucralose decreases or inhibits midodrine degradation by at least 30 percent at pH 5.0 after being stored for 3 months at 25 degrees Centigrade and 60% relative humidity when compared to the same midodrine solution stored under the same condition but without sucralose. In yet another embodiment of the invention, the sucralose decreases or inhibits midodrine degradation by at least 14 percent at pH 8.0 after being stored for 3 months at 25 degrees Centigrade and 60% relative humidity when compared to the same midodrine solution stored under the same condition but without sucralose.

Furthermore, the sucralose decreases or inhibits midodrine degradation by at least 14 percent at pH 3.5 after being stored for 1 months at 50 degrees Centigrade and ambient humidity when compared to the same midodrine solution stored under the same condition but without sucralose.

In addition, the sucralose decreases or inhibits midodrine degradation by at least 5 percent at pH 3.5 after being stored for 3 months at 40 degrees Centigrade and 75% relative humidity when compared to the same midodrine solution stored under the same condition but without sucralose.

In another embodiment of the invention, the sucralose decreases or inhibits midodrine degradation by at least 7 percent at pH 3.5 after being stored for 3 months at 30 degrees Centigrade and 65% relative humidity when compared to the same midodrine solution stored under the same condition but without sucralose. In another embodiment, the sucralose decreases or inhibits midodrine degradation by at least 25 percent at pH 3.5 after being stored for 3 months at 25 degrees Centigrade and 60% relative humidity when compared to the same midodrine solution stored under the same condition but without sucralose.

The invention further provides a stable, oral liquid formulation of midodrine HCL comprising midodrine HCL and a sucralose, wherein no more than about 10% by weight of the degradation product of midodrine HCL is present at commercially relevant stability conditions including, e.g., being stored for about 3-6 months at 40 degrees Centigrade or at least 2 years at 25° C.

In one embodiment, the formulation may have no more than 10% degradation product of midodrine during storage. In another embodiment, the formulation may have a shelf life of at least 3 months with no more than 10% degradation product of midodrine during storage. In another embodiment, the formulation may have a shelf life of at least 6 months with no more than 10% degradation product of midodrine during storage. In yet another embodiment, the formulation may have a shelf life of at least 1 year with no more than 10% degradation product of midodrine during storage. In a further embodiment, the formulation may have a shelf life of at least 2 years with no more than 10% degradation product of midodrine during storage.

In some embodiments of the invention, storage maybe at room temperature and ambient humidity. In one embodiment of the invention, the formulation is stored protected from light or stored in a light tight container.

Additionally, the invention also provides a stable, oral liquid formulation of midodrine HCL comprising midodrine HCL and a sucralose, wherein no more than about 1.1% by weight of the degradation product of midodrine HCL is present at for pH 3.5 formulation after storage at 25 degrees Centigrade and 60% relative humidity for 6 months.

In a particular embodiment of the invention, the composition is a midodrine hydrochloride oral solution which comprises midodrine hydrochloride, sucralose, methylparaben, propylparaben, flavoring, and hydrochloric acid and optionally a base. In accordance with the practice of the invention, the midodrine HCL may be admixed with sucralose. In an embodiment, the base is used to adjust pH of the formulation. In one embodiment, the base may be sodium hydroxide. In one embodiment of the invention, the formulation additionally comprises hydrochloric acid. In another embodiment of the invention, the formulation is acidic.

In one embodiment, sucralose decreases degradation of midodrine over a range of pH from 4.0 to 8.0 than the same formulation lacking sucralose. In a further embodiment, sucralose is more effective at decreasing degradation of midodrine than maltitol, xylitol or sorbitol over a range of pH from 4.0 to 5.0.

Additionally, the formulation may further comprise one or more preservative(s). Examples of suitable preservatives include, but are not limited to, methylparaben, ethylparaben, butylparaben, propylparaben, ethylenediaminetetraacetic acid (EDTA), sorbic acid and benzoic acid including salts thereof. Other preservatives can include any of butylated hydroxyl anisole, butylated hydroxyl toluene. In a preferred embodiment, the preservative is methylparaben or propylparaben or combination thereof. A suitable example of a salt of methylparaben is sodium methylparaben. A suitable example of a salt of propylparaben is sodium propylparaben. A suitable example of a salt of butylparaben is sodium butylparaben. A suitable example of a salt of a sorbic acid is a sodium or potassium sorbate. In one embodiment, the preservative(s) is selected from the group consisting of methylparaben, propylparaben, EDTA and sodium benzoate. In a preferred embodiment, the preservative(s) are methylparaben and propylparaben or salt thereof.

In one embodiment of the invention, the formulation comprises a racemic mixture of midodrine. (±)-2-amino-N-(β-hydroxy-2,5-dimethoxyphenethyl)acetamide. In one embodiment of the invention, in the formulation, at least 90% w/w such as, e.g., at least 95% w/w, at least 97% w/w, at least 98% w/w, at least 99% w/w of midodrine is present in the therapeutically active enantiomeric form, (−)-enantiomer of midodrine or (−)-2-amino-N(β-hydroxy-2,5-dimethoxyphenethyl)acetamide. In another further embodiment, midodrine is present in the form of a pharmaceutically acceptable salt such as a salt formed between midodrine and an inorganic acid. Suitable examples of inorganic acids include, but are not limited to hydrochloric acid, a carbonic acid, a hydrobromic acid, a hydroiodic acid, a nitric acid, a nitrous acid, a phosphorous acid, a phosphoric acid, a sulfuric acid and a peroxysulfuric acid and a combination thereof. In one embodiment, midodrine is a midodrine hydrochloride salt, a midodrine hydrobromide salt, a midodrine hydroiodide salt, a midodrine nitrate salt, a midodrine nitrite salt, a midodrine $H_3PO_3$ salt, a midodrine $H_3PO_4$ salt, a midodrine $H_2SO_3$ salt, a midodrine sulfate salt or a midodrine $H_2SO_5$ salt or a combination thereof.

In another further embodiment, midodrine may be present in the form of a pharmaceutically acceptable salt such as a salt formed between midodrine and an organic acid. Suitable examples of organic acids include, but are not limited to, acetic acid, propanoic acid, butyric acid, pentanoic acid, oxalic acid, malonic acid, succinic acid, glutaric acid, adipic acid, pimelic acid, fumaric acid, maleic acid, lactic acid, citric acid, tartaric acid, ascorbic acid, benzoic acid, salicylic acid and phthalic acid and a combination thereof. In one embodiment, midodrine is a midodrine $H_2CO_3$ salt, midodrine acetic acid salt, midodrine $C_2H_5COOH$ salt, midodrine $C_3H_7COOH$ salt, midodrine $C_4H_9COOH$ salt, midodrine $(COOH)_2$ salt, midodrine $CH_2(COOH)_2$ salt, midodrine $C_2H_4(COOH)_2$ salt, midodrine $C_3H_6COOH)2$ salt, midodrine $C_4H_8(COOH)_2$ salt, midodrine $C_5H_{10}(COOH)_2$ salt, midodrine fumaric acid salt, midodrine maleic acid salt, midodrine lactic acid salt, midodrine citric acid salt, midodrine tartaric acid salt, midodrine ascorbic acid salt, midodrine benzoic acid salt, midodrine salicylic acid salt or midodrine phthalic acid salt or a combination thereof.

In a preferred embodiment of the invention, the formulation comprises midodrine hydrochloride. In one embodiment, the formulation comprises a racemic mixture of midodrine hydrochloride, (±)-2-amino-N-(β-hydroxy-2,5-dimethoxyphenethyl)acetamide hydrochloride or (±)-2-amino-N-(β-hydroxy-2,5-dimethoxyphenethyl)acetamide HCL.

In one embodiment of the invention, the formulation maybe free or substantially free of added alcohol. In a further embodiment, the alcohol is an alkanol. In another embodiment, the alcohol is ethanol.

In one embodiment, the formulation is essentially or substantially free of ethanol. In one embodiment, the formulation additionally comprises less than 10% ethanol or comprises no ethanol. In one embodiment, the formulation additionally comprises less than 10% ethanol, less than 5% ethanol, less than 2.5% ethanol, less than 1% ethanol, less than 0.1% ethanol or no ethanol. In one embodiment, the formulation is essentially free of alcohol. In one embodiment, the formulation is essentially free of alkanol. In one embodiment, the formulation is essentially free of an alcohol including sugar alcohol or polyol. In one embodiment, the alcohol is ethanol.

In one embodiment, the formulation is essentially free or substantially free of a sugar sweetener. Suitable examples of sugar sweeteners include, but are not limited to, dextrose, fructose, sucrose, lactose, mannose, ribose, galactose and maltose.

In another embodiment of the invention, the formulation is free of a purified sugar. In yet another embodiment, the formulation is free of sugar alcohol or polyol.

In one embodiment of the invention, the sweetener decreases degradation of midodrine in the formulation over a range of pH from 3.0 to 8.0. In a further embodiment, the sweetener decreases degradation of midodrine in the formulation over a range of pH from 4.0 to 8.0. Further still, in another embodiment, the sweetener decreases degradation of midodrine in the formulation over a range of pH from 3.0 to 7.0.

In an embodiment, the formulation is essentially free or substantially free of a polyol sweetener or a sugar alcohol sweetener. Suitable examples of polyol sweeteners or sugar alcohol sweeteners include, but are not limited to maltitol, xylitol, sorbitol, mannitol, lactitol, erythritol, maltitol syrup, sorbitol syrup and glycerol.

In one embodiment, the formulation comprises a sweetener, wherein the sweetener is an artificial or non-nutritive sweetener. Suitable examples of artificial or non-nutritive sweeteners include, but are not limited to, sucralose, aspartame, acesulfame, neotame, advantame, steviol glycoside, Luo Han Guo fruit extract, a pharmaceutically acceptable salt thereof and a combination thereof. In one embodiment, the steviol glycoside is selected from the group consisting of stevioside, rebaudioside A, rebaudioside B, rebaudioside C, rebaudioside D, rebaudioside E, dulcoside A, a pharmaceutically acceptable salt thereof and a combination thereof. In one embodiment, the steviol glycoside is selected from the group consisting of stevioside, rebaudioside A, rebaudioside B, rebaudioside C, rebaudioside D, rebaudioside E and dulcoside A and a combination thereof. In a preferred embodiment of the invention, the sweetener may stabilize midodrine or midodrine hydrochloride in the stable, oral liquid formulation, preventing or inhibiting degradation of midodrine or midodrine hydrochloride. In one embodiment, the sweetener may stabilize midodrine or midodrine hydrochloride in a liquid formulation comprising methylparaben, propylparaben, a flavor, HCl and/or NaOH. In another embodiment, the sweetener may stabilize midodrine or midodrine hydrochloride in a liquid formulation comprising methylparaben, propylparaben, an orange vanilla flavor, HCl and/or NaOH. In one embodiment, the sweetener may stabilize midodrine or midodrine hydrochloride in a liquid formulation consisting of midodrine or midodrine hydrochloride, methylparaben, propylparaben, a flavor, HCl and/or NaOH. In another embodiment, the sweetener may stabilize midodrine or midodrine hydrochloride in a liquid formulation consisting of midodrine or midodrine hydrochloride, methylparaben, propylparaben, an orange vanilla flavor, HCl and/or NaOH. In an embodiment, the sweetener is aspartame. In one embodiment, the sweetener is aspartame and the liquid formulation comprises the ingredients as provided in Table 1. In one embodiment, the sweetener is aspartame and the liquid formulation has a composition as provided in Table 1. In one embodiment, the sweetener is aspartame and may stabilize the liquid formulation or decrease/inhibit midodrine degradation in the formulation with characteristics as provided in Table 4, 5 and/or 6 and/or FIG. 1. In a preferred embodiment, the sweetener is sucralose. In one embodiment, the sweetener is sucralose and the liquid formulation comprises the ingredients as provided in Table 1, 10, 13 or 14. In one embodiment, the sweetener is sucralose and the liquid formulation has a composition as provided as provided in Table 1, 10, 13 or 14. In one embodiment, the sweetener is sucralose and may stabilize the liquid formulation or decrease/inhibit midodrine degradation in the formulation with characteristics as provided in Table 4, 5, 6, 7, 8, 9, 11 and/or 12 and/or FIG. 1, 2 and/or 3. In one embodiment, the formulation is essentially free or substantially free of an artificial sweetener other than sucralose.

In one embodiment, the formulation comprises a sweetener, wherein the sweetener is a natural sweetener. Suitable examples of natural sweeteners include, but are not limited to stevia, molasses, molasses extract, agave syrup, orange syrup, raspberry syrup, concentrated raspberry juice, concentrated peppermint emulsion, anise water, concentrated camphor water, vanilla extract and liquorice liquid extract. In an embodiment, the natural sweetener may stabilize midodrine or midodrine hydrochloride in the stable, oral liquid formulation, preventing or inhibiting degradation of midodrine or midodrine hydrochloride. In one embodiment, the sweetener may stabilize midodrine or midodrine hydrochloride in a liquid formulation comprising methylparaben, propylparaben, a flavor, HCl and/or NaOH. In another embodiment, the sweetener may stabilize midodrine or midodrine hydrochloride in a liquid formulation comprising methylparaben, propylparaben, an orange vanilla flavor, HCl and/or NaOH. In one embodiment, the sweetener may stabilize midodrine or midodrine hydrochloride in a liquid formulation consisting of midodrine or midodrine hydrochloride, methylparaben, propylparaben, a flavor, HCl and/or NaOH. In another embodiment, the sweetener may stabilize midodrine or midodrine hydrochloride in a liquid formulation consisting of midodrine or midodrine hydrochloride, methylparaben, propylparaben, an orange vanilla flavor, HCl and/or NaOH. In one embodiment, the formulation is essentially free or substantially free of a natural sweetener.

In one embodiment, the formulation comprises a combination of one or more sweeteners. In one embodiment, the formulation comprises a combination of one or more sweeteners, wherein one of the sweeteners may be a flavor. In one embodiment, the formulation comprises a combination of one or more sweeteners, wherein none of the sweeteners is a flavor.

In one embodiment, the sweetener that stabilizes midodrine in the composition is an artificial sweetener. In a preferred embodiment, the sweetener that stabilizes midodrine in the composition is an artificial sweetener, wherein the artificial sweetener is sucralose.

Essentially free or substantially free in the context of the formulations of the invention includes formulations that may contain trace amounts of the undesirable agents. Thus, formulations which are essentially or substantially free of ethanol or non-sweetener alcohol include formulations having less than about 0.5%-1.0% of ethanol or non-sweetener alcohol (by weight), preferably less than 0.1% of ethanol or non-sweetener alcohol (by weight).

In one embodiment, the formulation is essentially or substantially free of desglymidodrine added to the formulation. In another embodiment, any desglymidodrine in the formulation is formed by hydrolysis of midodrine in situ to desglymidodrine. In another embodiment, hydrolysis of midodrine in situ to desglymidodrine is less than 10% of total midodrine used in the formulation. In another embodiment, hydrolysis of midodrine in situ to desglymidodrine is less than 4%, 2%, 1%, 0.5% or 0.1% of total midodrine used in the formulation. In another embodiment, hydrolysis of midodrine in situ to desglymidodrine is not detectable.

In an embodiment of the invention, the formulation is essentially or substantially free of a cyclamate and its salt. Suitable examples of a salt of cyclamate include, but are not limited to, calcium cyclamate, sodium cyclamate, magnesium cyclamate and potassium cyclamate.

In an embodiment of the invention, the formulation additionally comprises one or more preservatives. In one embodiment, the preservative is a parahydroxybenzoate. Suitable examples of parahydroxybenzoate include, but are not limited to, methyl parahydroxybenzoate, propyl parahydroxybenzoate and butyl parahydroxybenzoate.

In an embodiment of the invention, the formulation is essentially or substantially free of a preservative. In one embodiment, the formulation is essentially or substantially free of parahydroxybenzoate as a preservative. Suitable examples of parahydroxybenzoate include, but are not limited to, methyl parahydroxybenzoate, propyl parahydroxybenzoate and butyl parahydroxybenzoate.

In one embodiment of the invention, the formulation additionally comprises a weak organic acid. In one embodiment, the weak organic acid is free and not associated with midodrine as a midodrine organic acid salt. Suitable examples of weak organic acids include, but are not limited to, acetic acid, propanoic acid, butyric acid, pentanoic acid, oxalic acid, malonic acid, succinic acid, glutaric acid, adipic acid, pimelic acid, fumaric acid, maleic acid, lactic acid, citric acid, tartaric acid, ascorbic acid, benzoic acid, salicylic acid and phthalic acid.

In one embodiment of the invention, the formulation is essentially or substantially free of a weak organic acid, which if present in the formulation, is through introduction to the formulation as a pharmaceutically acceptable salt of midodrine. Suitable examples of weak organic acids include, but are not limited to, acetic acid, propanoic acid, butyric acid, pentanoic acid, oxalic acid, malonic acid, succinic acid, glutaric acid, adipic acid, pimelic acid, fumaric acid, maleic acid, lactic acid, citric acid, tartaric acid, ascorbic acid, benzoic acid, salicylic acid and phthalic acid.

In one embodiment, the viscosity of the solution is not more than 50 centipoise (cP).

In one embodiment, the formulation is essentially free of a metal chelator. In another embodiment, the formulation additionally comprises a metal chelator. Suitable examples of metal chelators include, but are not limited to, EDTA and EGTA.

In one embodiment, no more than about 10% by weight of the degradation product of midodrine HCL is present at a commercially relevant temperature such as between 0 degrees C. and about 60 degrees C. for a commercially relevant period of time, e.g., after being stored for 1 month at 50 degrees Centigrade over a range of pH from 2.5 to 8.0.

In another embodiment, no more than about 2.5% by weight of the degradation product of midodrine HCL is present after being stored for 2 weeks at 50 degrees Centigrade at pH 8.0. In another embodiment, no more than about 8% by weight of the degradation product of midodrine HCL is present after being stored for 1 month at 50 degrees Centigrade at pH 8.0. In another further embodiment, no more than about 7% by weight of the degradation product of midodrine HCL is present after being stored for 3 months at 40 degrees Centigrade. In yet another embodiment, no more than about 3.5% by weight of the degradation product of midodrine HCL is present after being stored for 3 months at 25 degrees Centigrade. Exemplary range of pH of the formulation is from about 2.5 to 8.0. In one embodiment, no more than about 8% by weight of the degradation product of midodrine HCL is present after being stored for 1 month at 50 degrees Centigrade over a range of pH from 2.5 to 8.0. In another embodiment, no more than about 7% by weight of the degradation product of midodrine is present after being stored for 3 months at 40 degrees Centigrade over a range of pH from 2.5 to 8.0. In yet another embodiment, no more than about 3.5% by weight of the degradation product of midodrine is present after being stored for 3 months at 25 degrees Centigrade over a range of pH from 2.5 to 8.0. In one embodiment, no more than about 10% by weight of the degradation product of midodrine HCL is present after being stored for 1 month at 50 degrees Centigrade over a range of pH from 2.5 to 8.0.

In one embodiment of the invention, no more than about 3.0% by weight of the degradation product of midodrine is present after being stored for 3 months at 25 degrees Centigrade over a range of pH from 3.5 to 8.0. In another embodiment, no more than about 0.5% by weight of the degradation product of midodrine is present after being stored for 3 months at 25 degrees Centigrade over a range of pH from 3.5 to 5.0. In yet another embodiment, no more than about 6.5% by weight of the degradation product of midodrine is present after being stored for 6 months at 40 degrees Centigrade for a formulation with an initial starting pH of 3.5. In a further embodiment, no more than about 1.8% by weight of the degradation product of midodrine is present after being stored for 6 months at 30 degrees Centigrade for a formulation with an initial starting pH of 3.5. In yet a further embodiment, no more than about 1.1% by weight of the degradation product of midodrine is present after being stored for 6 months at 25 degrees Centigrade for a formulation with an initial starting pH of 3.5.

In another further embodiment, no more than about 0.7% by weight of the degradation product of midodrine HCL is present after being stored for 1 month at 40 degrees Centigrade at pH 2.5. In another embodiment, no more than about 0.65% by weight of the degradation product of midodrine HCL is present after being stored for 1 month at 40 degrees Centigrade at pH 2.5. In another further embodiment, no more than about 0.60% by weight of the degradation product of midodrine HCL is present after being stored for 1 month at 40 degrees Centigrade at pH 2.5. In another embodiment, the degradation product of midodrine HCL present is about 0.59% by weight after being stored for 1 month at 40 degrees Centigrade at pH 2.5. In one embodiment, sucralose stabilizes the formulation over a range of pH from 3.0 to 8.0 than the same formulation without sucralose.

In one embodiment, midodrine is midodrine HCL and no more than about 3% by weight of the degradation product of midodrine HCL is present after being stored for 1 month at 50 degrees Centigrade at pH 2.5. In another embodiment, no more than about 5% by weight of the degradation product of midodrine HCL is present after being stored for 1 month at 50 degrees Centigrade at pH 4.0. In yet another embodiment, no more than about 4% by weight of the degradation product of midodrine HCL is present after being stored for 1 month at 50 degrees Centigrade at pH 4.0. In another embodiment, no more than about 4% by weight of the degradation product of midodrine HCL is present after being stored for 1 month at 50 degrees Centigrade at pH 5.0. In one embodiment, no more than about 2.5% by weight of the degradation product of midodrine HCL is present after being stored for 2 weeks at 50 degrees Centigrade at pH 8.0. In another embodiment, no more than about 10% by weight of the degradation product of midodrine HCL is present after being stored for 1 month at 50 degrees Centigrade at pH 8.0. In another embodiment, no more than about 8.0% by weight of the degradation product of midodrine HCL is present after being stored for 1 month at 50 degrees Centigrade at pH 8.0. In yet another embodiment, no more than about 1.0% by weight of the degradation product of midodrine HCL is present after being stored for 1 month at 40 degrees Centigrade at pH 2.5. In another embodiment, no more than about 2.4% by weight of the degradation product of midodrine HCL is present after being stored for 3 months at 40 degrees Centigrade at pH 2.5. In yet another embodiment, no more than about 3.7% by weight of the degradation product of midodrine HCL is present after being stored for 3 months at 40 degrees Centigrade at pH 4.0. In a further embodiment, no more than about 3.5% by weight of the degradation product of midodrine HCL is present after being stored for 3 months at 40 degrees Centigrade at pH 5.0. In one embodiment, no more than about 0.8% by weight of the degradation product of midodrine HCL is present after being stored for 3 months at 25 degrees Centigrade at pH 2.5. In another embodiment, no more than about 0.8% by weight of the degradation product of midodrine HCL is present after being stored for 3 months at 25 degrees Centigrade at pH 4.0. In yet another embodiment, no more than about 0.7% by weight of the degradation product of midodrine HCL is present after being stored for 3 months at 25 degrees Centigrade at pH 5.0. In a further embodiment, no more than about 3.4% by weight of the degradation product of midodrine HCL is present after being stored for 3 months at 25 degrees Centigrade at pH 8.0.

In one embodiment of the invention, the midodrine is midodrine HCL and no more than about 6.5% by weight of the degradation product of midodrine HCL is present after being stored for 6 months at 40 degrees Centigrade for a formulation with an initial starting pH of 3.5. In one embodiment, the formulations of midodrine is midodrine HCL and no more than about 1.8% by weight of the degradation product of midodrine HCL is present after being stored for 6 months at 30 degrees Centigrade for a formulation with an initial starting pH of 3.5. In another embodiment, the formulations of midodrine is midodrine HCL and no more than about 1.1% by weight of the degradation product of midodrine HCL is present after being stored for 6 months at 25 degrees Centigrade for a formulation with an initial starting pH of 3.5.

In an embodiment, the midodrine HCL and sucralose are present in the formulation in a midodrine HCL:sucralose ratio (w/w) of about 2.5:1 to about 1:35. In another embodiment, the midodrine HCL and sucralose are present in the formulation in a midodrine HCL:sucralose ratio (w/w) of about 1:1 to about 1:10. In a preferred embodiment, the midodrine HCL and sucralose are present in the formulation in a midodrine HCL:sucralose ratio (w/w) of about 1:4. In an embodiment, the formulation comprises up to about 5 mg of sucralose for about 0.5 mg of midodrine HCL. In a preferred embodiment, the formulation comprises up to about 2 mg of sucralose for about 0.5 mg of midodrine HCL. In another embodiment, no more than about 10% by weight of the degradation product of midodrine HCL is present after being stored for 1 month at 50 degrees Centigrade over a range of pH from 2.5 to 8.0.

In one embodiment of the invention, no more than about 8% by weight of the degradation product of midodrine HCL is present after being stored for 1 month at 50 degrees Centigrade over a range of pH from 2.5 to 8.0. In another embodiment, no more than about 7% by weight of the degradation product of midodrine HCL is present after being stored for 3 months at 40 degrees Centigrade over a range of pH from 2.5 to 8.0. In yet another embodiment, no more than about 3.5% by weight of the degradation product of midodrine HCL is present after being stored for 3 months at 25 degrees Centigrade over a range of pH from 2.5 to 8.0. In a further embodiment, no more than about 3.0% by weight of the degradation product of midodrine HCL is present after being stored for 3 months at 25 degrees Centigrade over a range of pH from 3.5 to 8.0 In an additional embodiment, no more than about 0.5% by weight of the degradation product of midodrine HCL is present after being stored for 3 months at 25 degrees Centigrade over a range of pH from 3.5 to 5.0 In another embodiment, no more than about 6.5% by weight of the degradation product of midodrine HCL is present after being stored for 6 months at 40 degrees Centigrade for a formulation with an initial starting pH of 3.5. Further still, in one embodiment, no more than about 1.8% by weight of the degradation product of midodrine HCL is present after being stored for 6 months at 30 degrees Centigrade for a formulation with an initial starting of 3.5. In another embodiment, no more than about 1.1% by weight of the degradation product of midodrine HCL is present after being stored for 6 months at 25 degrees Centigrade for a formulation with an initial starting pH of 3.5.

In another embodiment, the formulation is stored at 40° C.±2° C. and relative humidity of 75%±5%.

In one embodiment of the invention, the formulation is stored at 50° C.±2° C. and ambient humidity. Also, in an embodiment of the invention, the pH of the formulation may be least pH 3 or greater. In a further embodiment, the pH of the formulation may be least pH 3.5 or greater. Further still, in one embodiment, the pH of the formulation may be least pH 4.0 or greater. In yet a further embodiment, the pH of the formulation may be least pH 4.5 or greater. Additionally, in an embodiment, the pH of the formulation may be least pH 5.0 or greater. In a further embodiment, the pH of the formulation may be least pH 5.5 or greater. Further yet, in another embodiment, the pH of the formulation may be least pH 6.0 or greater. In another embodiment, the pH of the formulation may be least pH 6.5 or greater.

In one embodiment, the pH of the formulation is pH 8.0 or lower. In a further embodiment, the pH of the formulation is pH 7.5 or lower. Further yet, in an embodiment, the pH of the formulation is pH 7.0 or lower. In another embodiment, the pH of the formulation is between pH 3.0 and 7.0. In yet another embodiment, the pH of the formulation is between pH 3.5 and 6.5. Additionally, in another embodiment, the pH of the formulation is between pH 4.0 and 6.0.

In one embodiment, pH of the formulation changes during storage. In another embodiment, change in pH of the formulation during storage is toward pH 6 or 7.

In a further embodiment, the change in pH of the formulation during storage is toward pH 5.6±0.2. In another further embodiment, pH of the formulation is 3.5±0.1 and wherein sucralose either decreases or does not promote degradation of midodrine.

In yet another embodiment, the ratio (w/w) of midodrine HCL to Sucralose is about 1:4. In yet a further embodiment, the formulation has a pH anywhere in the range of 2.5 to 8.0. In a further embodiment, the sucralose inhibits midodrine degradation by about 0.2% or at least 0.1% of total midodrine used in the formulation.

In yet another embodiment, the formulation has a pH anywhere in the range of 3.5 to 6.0. In another embodiment, the formulation has a pH anywhere in the range of 3.0 to 6.0. In another embodiment, the formulation has a pH anywhere in the range of 3.0 to 5.0. In a preferred embodiment, the formulation has a pH of about 5.0. In a separate preferred embodiment, the formulation has a pH of about 4.0. In a separate preferred embodiment, the formulation has a pH of about 3.0.

Also, in another embodiment, the formulation has a pH of about 2.5 to 4.0. In yet another embodiment, the formulation has a pH of about 2.5 to 5.0. In yet another embodiment, the formulation has a pH of about 3.5 to 4.0. In a preferred embodiment, the formulation has a pH of about 3.5. In a separate preferred embodiment, the formulation has a pH of about 4.5.

In a further embodiment the formulation has a ratio of moles of midodrine HCL to sucralose of less than 3:1. In another embodiment, the formulation has a ratio of moles of midodrine HCL to sucralose of more than 1:25. In another embodiment, the formulation has a ratio of moles of midodrine HCL to sucralose of less than 3:1 but more than 1:25. In another embodiment, the formulation has a ratio of moles of midodrine HCL to sucralose of less than 1:1. In another embodiment, the formulation has a ratio of moles of midodrine HCL to sucralose of more than 1:9. In another embodiment, the formulation has a ratio of moles of midodrine HCL to sucralose of less than 1:1 but more than 1:9. In yet a preferred embodiment, the formulation has a ratio of moles of midodrine HCL to sucralose of about 1:3.

Exemplary dosage forms of midodrine HCL and sucralose include, but are not limited to, formulations comprising about 0.1 mg/ml to 20 mg/ml of midodrine HCL. In one embodiment, the formulation comprises about 0.5 mg/ml to 20 mg/ml midodrine HCL. In another embodiment, the formulation comprises about 0.5 mg/ml to 10 mg/ml midodrine HCL. In a preferred embodiment, the formulation comprises about 0.5 mg/mL of midodrine HCL. In one embodiment, the formulation comprises about $3.44 \times 10^{-4}$ M to $6.88 \times 10^{-2}$ M midodrine HCL. In one embodiment, the formulation comprises about $1.72\times10^{-3}$ M to $6.88\times10^{-2}$ M midodrine HCL. In one embodiment, the formulation comprises about $1.72\times10^{-3}$ M to $3.44\times10^{-2}$ M midodrine HCL. In another embodiment, the formulation has about $1.72\times10^{-3}$ M midodrine HCL. With regard to sucralose, in one embodiment, the formulation has about $5.03\times10^{-3}$ M sucralose.

In one particular embodiment of the invention, the amount of midodrine HCL is about 0.5 mg/ml and the amount of sucralose is about 2.0 mg/mL in the formulation. In another embodiment, the methylparaben is 1.8 mg/mL. In yet another embodiment, the propylparaben is 0.2 mg/mL. In an additional embodiment, the orange vanilla flavor is 1.5 mg/mL.

In another embodiment, the formulation comprises midodrine HCL and sucralose in a ratio in weight of midodrine HCL:sucralose which is 0.5 mg:2.0 mg with each value capable of varying by ±10%. In one embodiment, the midodrine is midodrine HCL and the ratio of moles of midodrine HCL to sucralose is greater than 1:4. In another embodiment, the midodrine is midodrine HCL and the ratio of moles of midodrine HCL to sucralose is less than 3:2. In yet a further embodiment, the formulation comprises a ratio of moles of midodrine HCL to sucralose which is greater than 1:4 and less than 3:2. In another embodiment, the midodrine HCL and sucralose are present in the formulation in a ratio of about 1:1 to about 1:10.

In one embodiment, no more than 1% by weight of the degradation product of midodrine is present after being stored for 1 month at 40 degrees Centigrade and 75% relative humidity at pH 2.5. In another embodiment, no more than 2.2% by weight of the degradation product of midodrine is present after being stored for 3 months at 40 degrees Centigrade and 75% relative humidity at pH 2.5. In yet another embodiment, no more than 3.5% by weight of the degradation product of midodrine is present after being stored for 3 months at 40 degrees Centigrade and 75% relative humidity at pH 4.0. Further, in another embodiment, no more than 3.4% by weight of the degradation product of midodrine is present after being stored for 3 months at 40 degrees Centigrade and 75% relative humidity at pH 5.0. In yet another embodiment, no more than 7.0% by weight of the degradation product of midodrine is present after being stored for 3 months at 40 degrees Centigrade and 75% relative humidity at pH 8.0.

The formulation is no more than about 3.0% by weight of the degradation product of midodrine is present after being stored for 1 months at 50 degrees Centigrade and ambient humidity for a formulation with an initial pH of 3.5. In a further embodiment, the sucralose inhibits midodrine degradation by about 0.6% or at least 0.4% of total midodrine used in the formulation.

In one embodiment, the formulation is no more than about 2.9% by weight of the degradation product of midodrine is present after being stored for 3 months at 40 degrees Centigrade and relative humidity of 75% for a formulation with an initial pH of 3.5. In a further embodiment, sucralose inhibits midodrine degradation by about 0.2% or at least 0.1% of total midodrine used in the formulation.

In another embodiment, the formulation is no more than about 6.5% by weight of the degradation product of midodrine is present after being stored for 6 months at 40 degrees Centigrade and relative humidity of 75% for a formulation with an initial pH of 3.5.

The formulation is no more than about 0.9% by weight of the degradation product of midodrine is present after being stored for 3 months at 30 degrees Centigrade and relative humidity of 65% for a formulation with an initial pH of 3.5. In a further embodiment, the sucralose inhibits midodrine degradation by about 0.1% of total midodrine used in the formulation.

In one embodiment, the formulation is no more than about 1.8% by weight of the degradation product of midodrine is present after being stored for 6 months at 30 degrees Centigrade and relative humidity of 65% for a formulation with an initial pH of 3.5. In another embodiment, the formulation is no more than about 1.1% by weight of the degradation product of midodrine is present after being stored for 6 months at 25 degrees Centigrade and relative humidity of 60% for a formulation with an initial pH of 3.5. In a further embodiment, the sucralose inhibits midodrine degradation or preserves midodrine by about 0.2% or at least 0.1%.

In yet another embodiment the formulation is no more than about 0.5% by weight of the degradation product of midodrine is present after being stored for 3 months at 25 degrees Centigrade and relative humidity of 60% for a formulation with an initial pH of 3.5. Additionally, in an embodiment, the midodrine is free or substantially free of desglymidodrine.

In one embodiment of the invention as described above, the sucralose serves as both a sweetener to increase palatability and a stabilizing agent of midodrine to inhibit or decrease midodrine degradation in the aqueous formulation. In another embodiment, the formulation comprises less than 10% of the degradation products of midodrine during storage at pH 3.0 to 8.0 for at least 6 months. In yet another embodiment, the formulation comprises less than 10% of the degradation products of midodrine during storage at pH 3.0 to 7.0 for at least 2 years.

In one embodiment of the invention, no more than about 1% by weight of the degradation product of midodrine HCL is present after being stored for 1 month at 40 degrees Centigrade. In one embodiment of the invention, no more than about 1% by weight of the degradation product of midodrine HCL is present after being stored for 1 month at 40 degrees Centigrade at pH 2.5. In one embodiment of the invention, no more than about 0.7% by weight of the degradation product of midodrine HCL is present after being stored for 1 month at 40 degrees Centigrade at pH 2.5. In one embodiment of the invention, no more than about 0.65% by weight of the degradation product of midodrine HCL is present after being stored for 1 month at 40 degrees Centigrade at pH 2.5. In one embodiment of the invention, no more than about 0.60% by weight of the degradation product of midodrine HCL is present after being stored for 1 month at 40 degrees Centigrade at pH 2.5. In one embodiment of the invention, the degradation product of midodrine HCL is about 0.59% after being stored for 1 month at 40 degrees Centigrade. In one embodiment of the invention, the degradation product of midodrine HCL is about 0.59% after being stored for 1 month at 40 degrees Centigrade at pH 2.5.

In an embodiment, the pH of the composition may be adjusted with an acid or a base as is known in the art. In an embodiment, the pH of the composition is adjusted with HCl. In an embodiment, the pH of the composition is adjusted with NaOH.

In one embodiment, the formulation comprises a sweetener at up to 55% (w/w) of the formulation. In one embodiment, the formulation comprises a sweetener at up to 55% (w/w) of the formulation, wherein the sweetener stabilizes midodrine in the composition. In one embodiment, the formulation comprises a sweetener at no more than 55% (w/w) of the formulation, wherein the sweetener stabilizes midodrine in the formulation and midodrine HCL comprises no more than 10% (w/w) of the formulation.

In one embodiment, the formulation comprises a sweetener at up to 20% (w/w) of the formulation. In one embodiment, the formulation comprises a sweetener at up to 20% (w/w) of the formulation, wherein the sweetener stabilizes midodrine in the composition. In one embodiment, the formulation comprises a sweetener at no more than 20% (w/w) of the formulation, wherein the sweetener stabilizes midodrine in the formulation and midodrine HCL comprises no more than 10% (w/w) of the formulation. In one embodiment, the sweetener is sucralose. In a preferred embodiment, the formulation comprises sucralose at about 0.2% (w/w) of the formulation, wherein the sucralose stabilizes midodrine in the formulation and midodrine HCL comprises about 0.05% (w/w) of the formulation. In a preferred embodiment, the formulation comprises sucralose at about 0.2% (w/v) of the formulation, wherein the sucralose stabilizes midodrine in the formulation and midodrine HCL comprises about 0.05% (w/v) of the formulation.

In one embodiment, the formulation comprises sucralose at no more than 200 mg/ml. In one embodiment, the formulation comprises sucralose at no more than 50 mg/ml. In one embodiment, the formulation comprises sucralose at no more than 20 mg/ml. In one embodiment, the formulation comprises sucralose at no more than 10 mg/ml. In one embodiment, the formulation comprises sucralose at more than 0.1 mg/ml. In one embodiment, the formulation comprises sucralose at more than 0.5 mg/ml. In one embodiment, the formulation comprises sucralose at more than 1 mg/ml. In one embodiment, the formulation comprises sucralose at about 2 mg/ml.

In one embodiment, the formulation comprises sucralose between about 0.1 mg/ml to 200 mg/ml. In one embodiment, the formulation comprises sucralose between about 1 mg/ml to 50 mg/ml. In one embodiment, the formulation comprises sucralose between about 1 mg/ml to 20 mg/ml. In one embodiment, the formulation comprises sucralose between about 1 mg/ml to 10 mg/ml. In one embodiment, the formulation comprises sucralose between about 1 mg/ml to 5 mg/ml. In one embodiment, the formulation comprises sucralose between about 1 mg/ml to 3 mg/ml. In one embodiment, the formulation comprises sucralose between about 1.5 mg/ml to 3 mg/ml. In one embodiment, the formulation comprises sucralose between about 1.5 mg/ml to 2.5 mg/ml.

In one embodiment, the formulation comprises midodrine HCL at no more than 10 mg/ml. In one embodiment, the formulation comprises midodrine HCL at no more than 5 mg/ml. In one embodiment, the formulation comprises midodrine HCL at no more than 2 mg/ml. In one embodiment, the formulation comprises midodrine HCL at no more than 1 mg/ml. In one embodiment, the formulation comprises midodrine HCL at no more than 0.75 mg/ml. In one embodiment, the formulation comprises midodrine HCL at more than 0.1 mg/ml. In one embodiment, the formulation comprises midodrine HCL at more than 0.2 mg/ml. In one embodiment, the formulation comprises midodrine HCL at more than 0.4 mg/ml. In one embodiment, the formulation comprises midodrine HCL at about 0.5 mg/ml.

In one embodiment, the formulation comprises midodrine HCL between about 0.1 mg/ml to 10 mg/ml. In one embodiment, the formulation comprises midodrine HCL between about 0.1 mg/ml to 5 mg/ml. In one embodiment, the formulation comprises midodrine HCL between about 0.1 mg/ml to 2 mg/ml. In one embodiment, the formulation comprises midodrine HCL between about 0.2 mg/ml to 10 mg/ml. In one embodiment, the formulation comprises midodrine HCL between about 0.2 mg/ml to 5 mg/ml. In one embodiment, the formulation comprises midodrine HCL between about 0.2 mg/ml to 2 mg/ml. In one embodiment, the formulation comprises midodrine HCL between about 0.2 mg/ml to 1 mg/ml. In one embodiment, the formulation comprises midodrine HCL between about 0.4 mg/ml to 1 mg/ml. In one embodiment, the formulation comprises midodrine HCL between about 0.4 mg/ml to 0.75 mg/ml.

The pharmaceutical compositions of the invention may be formulated as liquid dosage forms such as elixir, suspension or syrup.

The pharmaceutical compositions of the present invention may be mixed with pharmaceutically acceptable carriers, binders, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, coloring agent, dyes, preservatives and dispensing agents, or compounds of a similar nature depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety.

Pharmaceutically acceptable carriers are generally non-toxic to recipients at the dosages and concentrations employed and are compatible with other ingredients of the formulation. Examples of pharmaceutically acceptable carriers include water, saline, Ringer's solution, vegetable oils. fats, ethyl oleate, liposomes, waxes polymers, including gel forming and non-gel forming polymers, and suitable mixtures thereof. The carrier may contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; monosaccharides, disaccharides, and other carbohydrates including cellulose or its derivatives (so long as they do not destabilize midodrine or midodrine hydrochloride); chelating agents such as EDTA; counterions such as sodium; and/or nonionic surfactants such as polysorbates, poloxamers, or PEG.

In an embodiment, the carrier is water. In one embodiment, the carrier is an aqueous carrier or purified water. In an embodiment, the formulation comprises a carrier, wherein the carrier is water. In an embodiment, the formulation comprises a carrier, wherein the carrier comprises water and less than 10% alcohol. In an embodiment, the formulation comprises a carrier, wherein the carrier comprises water and less than 5% alcohol. In an embodiment, the formulation comprises a carrier, wherein the carrier comprises water and less than 2% alcohol. In an embodiment, the formulation comprises a carrier, wherein the carrier comprises water and less than 1% alcohol. In an embodiment, the formulation comprises a carrier, wherein the carrier comprises water and less than 0.1% alcohol. In one embodiment, the alcohol is an alkanol. In one embodiment, the alcohol has a chemical formula of $(CH)_3(CH)_nOH$, wherein n is a non-negative integer. In one embodiment, the alcohol is ethanol. In one embodiment, the alcohol is not a sugar alcohol or a polyol.

In one embodiment, the formulation additionally comprises water. In one embodiment, the formulation additionally comprises water and less than 10% alcohol. In one embodiment, the formulation additionally comprises water and less than 5% alcohol. In one embodiment, the formulation additionally comprises water and less than 2% alcohol. In one embodiment, the formulation additionally comprises water and less than 1% alcohol. In one embodiment, the formulation additionally comprises water and less than 0.1% alcohol. In one embodiment, the alcohol is an alkanol. In one embodiment, the alcohol has a chemical formula of $(CH)_3(CH)_nOH$, wherein n is a non-negative integer. In one embodiment, the alcohol is ethanol. In one embodiment, the alcohol is not a sugar alcohol or a polyol.

In an embodiment, the formulation comprises a carrier free of alcohol. In an embodiment, the formulation comprises a carrier, wherein the carrier is water and free of alcohol. In one embodiment, the alcohol is ethanol. In an embodiment, the formulation comprises a carrier, wherein the carrier is water and free of alcohol and wherein the alcohol is ethanol. In one embodiment, the formulation additionally comprises water and is free of alcohol. In one embodiment, the formulation additionally comprises water and is free of ethanol. In one embodiment, the alcohol is not a sugar alcohol or a polyol. In one embodiment, the alcohol is an alkanol. In one embodiment, the alcohol has a chemical formula of $(CH)_3(CH)_nOH$, wherein n is a non-negative integer.

Examples of excipients include, but are not limited to, starch, surfactants, lipophilic vehicles, hydrophobic vehicles, pregelatinized starch, Avicel, lactose, milk sugar, sodium citrate, calcium carbonate, dicalcium phosphate, and lake blend purple.

Examples of wetting agents include, but are not limited to, propylene glycol monostearate, sorbitan monooleate, diethylene glycol monolaurate and polyoxyethylene laurel ether.

Examples of lubricants include magnesium or calcium stearate, sodium lauryl sulphate, talc, starch, lycopodium and stearic acid as well as high molecular weight polyethylene glycols.

Examples of buffering agents include acetates, phosphates, citrate, maleate, gluconates and borates.

Examples of coloring agents include, but are not limited to, any of the approved certified water soluble FD and C dyes, mixtures thereof; and water insoluble FD and C dyes suspended on alumina hydrate.

The artisan of ordinary skill in the art will recognize that many different ingredients can be used in formulations according to the present invention, in addition to midodrine and sucralose, while maintaining effectiveness of the formulations in treating the diseases and disorders described herein. The list provided herein is not exhaustive.

METHODS OF THE INVENTION

The invention provides a method for treating a patient suffering from orthostatic hypotension and/or urinary incontinence. In one embodiment the method comprises of administering an effective amount of midodrine in the form of a formulation of the invention to a patient in need thereof.

In one embodiment, urinary incontinence is urinary stress incontinence. In another embodiment an administration of the formulation takes place at wake-up time. In another further embodiment, an administration of the formulation takes place in the morning, middle of the day, and at least 6 hours before bedtime.

In one embodiment, an administration of the formulation is determined based on need of a subject in need.

In one embodiment, an administration of the formulation is one dose of the formulation, wherein one dose of the formulation is about 2.5 mg to 10 mg. In another embodiment, an administration of the formulation is between about 5 to 20 milliliters.

In one embodiment, the administration takes place 1 to 6 times daily. For example, a preferred dose is 10 mg, administered three times daily.

In accordance with the practice of the invention, dosing may take place during the daytime hours when the subject/patient needs to be upright, pursuing the activities of daily living. In one embodiment, a dosing schedule of approximately 4-hour intervals is as follows: shortly before, or upon arising in the morning, midday and late afternoon (not later than 6 pm). In another embodiment, doses may be given in 3-hour intervals, as needed, to control symptoms, but not more frequently. In yet another embodiment, single doses as high as 20 mg may be given to patients. In an additional embodiment, to reduce the potential for supine hypertension during sleep, a formulation of the invention may not be given after the evening meal or less than 4 hours before bedtime.

In a further embodiment, total daily doses greater than 30 mg may be given to the subject. In another embodiment, dosing in patients with abnormal renal function may be initiated using 2.5-mg doses.

The invention provides the method for treating a patient suffering from septic shock, the method comprising administering an effective amount of midodrine in the formulation to a patient in need thereof.

The invention provides method for treating a patient suffering from a condition responsive to alpha-1 adrenergic (A1) receptor stimulation, the method comprising administering an effective amount of midodrine in the formulation to a patient in need thereof.

The invention provides a method for treating a patient suffering from syncope, the method comprising administering an effective amount of midodrine in the formulation to a patient in need thereof.

The invention provides, a method of alleviating symptomatic orthostatic hypotension in a patient in need thereof comprising administering to the patient an effective amount of a formulation of the invention.

In accordance with the practice of the invention, the drug can be administered one or more times a day, daily, weekly, monthly or yearly.

Dosage of the therapeutic agent(s) of the invention is dependent upon many factors including, but not limited to, the type of tissue affected, the type of disease being treated, the severity of the disease, a subject's health and response to the treatment with the agents. Accordingly, dosages of the agents can vary depending on each subject and the mode of administration. In accordance with the practice of the invention, the subject or patient may be a mammal. In other embodiments of the invention, the subject may be any of human, monkey, ape, dog, cat, cow, horse, sheep, rabbit, mouse, or rat.

The invention further provides methods of increasing blood pressure in a subject. In one embodiment, the method comprises administering to the subject an effective amount of any of the liquid formulations of the invention comprising: (a) midodrine or midodrine hydrochloride; and (b) sucralose in an effective amount so as to increase blood pressure in the subject. Merely by way of example, the patient may be suffering from a disorder associated with hypotension. For example, the disorder associated with hypotension may be an autonomous nervous system disorder. Examples of autonomous nervous system disorders include neurogenic orthostatic hypotension; symptomatic orthostatic hypotension; or symptomatic hypotension.

In a preferred embodiment, the midodrine is a midodrine HCL. In accordance with the invention, the midodrine may be midodrine base. In one embodiment, the midodrine is a pharmaceutically acceptable salt of midodrine. The pharmaceutically acceptable salt of midodrine may be a salt formed between midodrine and an inorganic acid. Examples of inorganic acids include any of hydrochloric acid, a carbonic acid, a hydrobromic acid, a hydroiodic acid, a nitric acid, a nitrous acid, a phosphorous acid, a phosphoric acid, a sulfuric acid and a peroxysulfuric acid or a combination thereof. In one embodiment, the pharmaceutically acceptable salt of midodrine is a salt formed between midodrine and an organic acid. Examples of suitable organic acids include any of acetic acid, propanoic acid, butyric acid, pentanoic acid, oxalic acid, malonic acid, succinic acid, glutaric acid, adipic acid, pimelic acid, fumaric acid, maleic acid, lactic acid, citric acid, tartaric acid. ascorbic acid, benzoic acid, salicylic acid or phthalic acid or a combination thereof.

Additionally, in the liquid formulations of the invention, the midodrine is free or substantially free of desglymidodrine. In one embodiment, the desglymidodrine may be formed in situ during storage of the midodrine solution.

The invention also provides methods of stabilizing midodrine dissolved in an aqueous solution comprising introducing an artificial or non-nutritive sweetener to the midodrine solution so as to obtain an artificial or non-nutritive sweetener-midodrine solution. The artificial or non-nutritive sweetener may inhibit or reduce degradation of midodrine, thereby stabilizing the midodrine dissolved in the aqueous solution.

Examples of artificial or non-nutritive sweeteners in the midodrine solution/formulation of the invention include sucralose, aspartame, acesulfame, neotame, and advantame, steviol glycoside, Luo Han Guo fruit extract, or a pharmaceutically acceptable salt thereof and/or a combination thereof. Examples of a steviol glycoside includes any of stevioside, rebaudioside A, rebaudioside B, rebaudioside C, rebaudioside D, rebaudioside E, dulcoside A, or a pharmaceutically acceptable salt thereof and/or a combination thereof. In a particular example, the artificial or non-nutritive sweetener may be any of sucralose, aspartame, or a pharmaceutically acceptable salt thereof and/or a combination thereof. In a specific embodiment, the artificial or non-nutritive sweetener may be aspartame or a pharmaceutically acceptable salt thereof. In a preferred embodiment, the artificial or non-nutritive sweetener is sucralose or a pharmaceutically acceptable salt thereof.

In accordance with the practice of the invention, the midodrine solution/formulation of the invention used in the methods of the invention may additionally comprise a preservative. The preservative may include any of methylparaben, ethylparaben, butylparaben, propylparaben, ethylenediaminetetraacetic acid (EDTA), sorbic acid, benzoic acid, sodium benzoate or a pharmaceutically acceptable salt thereof. In a specific embodiment, the preservative is a paraben. Examples of suitable parabens include methylparaben, ethylparaben, propylparaben, butylparaben or a pharmaceutically acceptable salt thereof.

Suitable examples of the preservative may include, but are not limited to, methylparaben, ethylparaben, propylparaben, butylparaben, sodium benzoate and a combination thereof. In one embodiment, the preservative is a combination of methylparaben and propylparaben. In another embodiment, the preservative is a combination of methylparaben and propylparaben.

The pH of the midodrine solution/formulation of the invention used in the methods of the invention may be adjusted with an acid and/or a base. In one embodiment of the invention, the formulation is adjusted to a pH between pH 2.5 and 8.0 with HCl and/or NaOH. In another embodiment, the formulation has a pH between 3.0 and 7.0. In another embodiment, the formulation has a pH between 3.5 and 7.0. In yet another embodiment, the formulation has a pH between 3.5 and 6.0. Moreover, in an additional embodiment, the formulation has a pH between 4.0 and 5.0.

Examples of suitable acids include any of hydrochloric acid, phosphoric acid, phosphorous acid or a combination thereof. In a preferred embodiment, the acid may be HCl. Examples of suitable bases include any of NaOH, KOH or a combination thereof. In a preferred embodiment, the base may be NaOH.

The pH of the midodrine solution/formulation of the invention used in the methods of the invention may include any of about 3.0±0.1, 3.1±0.1, 3.2±0.1, 3.3±0.1, 3.4±0.1, 3.5±0.1, 3.6±0.1, 3.7±0.1, 3.8±0.1, 3.9±0.1, 4.0±0.1, 4.1±0.1, 4.2±0.1, 4.3±0.1, 4.4±0.1, 4.5±0.1, 4.6±0.1, 4.7±0.1, 4.8±0.1, 4.9±0.1, 5.0±0.1, 5.1±0.1, 5.2±0.1, 5.3±0.1, 5.4±0.1, 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, and 7.0±0.1. In another embodiment, the pH of the midodrine solution/formulation of the invention may include any of 3.5±0.1, 3.6±0.1, 3.7±0.1, 3.8±0.1, 3.9±0.1, 4.0±0.1, 4.1±0.1, 4.2±0.1, 4.3±0.1, 4.4±0.1, 4.5±0.1, 4.6±0.1, 4.7±0.1, 4.8±0.1, 4.9±0.1, 5.0±0.1, 5.1±0.1, 5.2±0.1, 5.3±0.1, 5.4±0.1, 5.5±0.1, 5.6±0.1, 5.7±0.1, 5.8±0.1, 5.9±0.1, 6.0±0.1, 6.1±0.1, 6.2±0.1, 6.3±0.1, 6.4±0.1 and 6.5±0.1. In yet a further embodiment, the pH of the midodrine solution/formulation of the invention of 3.5±0.1, 3.6±0.1, 3.7±0.1, 3.8±0.1, 3.9±0.1, 4.0±0.1, 4.1±0.1, 4.2 ±0.1, 4.3±0.1, 4.4±0.1, 4.5±0.1, 4.6±0.1, 4.7±0.1, 4.8±0.1, 4.9±0.1, 5.0±0.1, 5.1±0.1, 5.2±0.1, 5.3±0.1, 5.4±0.1 and 5.5±0.1. In a specific embodiment, the pH of the midodrine solution/formulation of the invention may be any of 4.0±0.1, 4.1±0.1, 4.2±0.1, 4.3±0.1, 4.4±0.1, 4.5±0.1, 4.6±0.1, 4.7±0.1, 4.8±0.1, 4.9±0.1 and 5.0±0.1. In yet another specific embodiment, the pH of the midodrine solution/formulation of the invention may be about 3.0. In an additional embodiment, the pH of the midodrine solution/formulation of the invention may be about 3.5. In yet an additional embodiment, the pH of the midodrine solution may be about 4.0. Further, in one example the pH of the midodrine solution (also referred to herein as the formulation of the invention) may be about 4.5. In another example, the pH of the midodrine solution may be about 5.0.

In accordance with the invention, the midodrine solution comprises more than 95% by weight purified water. In another embodiment, the midodrine solution comprises more than 99% by weight purified water.

Also, in accordance with the invention, the midodrine solution used in the methods may additionally comprise less than about 1% ethanol, or less than about 0.1% ethanol or free of ethanol.

Further, in the methods of the invention, the midodrine solution may additionally comprise a flavor. Examples of suitable flavors include, but are not limited to, molasses, molasses extract, agave syrup, orange syrup, raspberry syrup, concentrated raspberry juice, concentrated peppermint emulsion, anise water, concentrated camphor water, liquorice liquid extract, vanilla extract, orange extract and orange-vanilla extract. In a preferred embodiment, the flavor may be orange-vanilla extract.

KITS OF THE INVENTION

In a further embodiment, the present invention provides kits (i.e., a packaged compositions of the invention with instructions) containing the active agents of the invention useful for treating the diseases and/or conditions described herein.

The kit can contain a pharmaceutical composition of the invention in liquid form and an acceptable carrier or adjuvant, e.g., pharmaceutically acceptable buffer, such as phosphate-buffered saline, Ringer's solution or dextrose solution. It may further include other materials desirable from a commercial and user standpoint, including package inserts with instructions for use.

The kit comprises one or more containers with a label and/or instructions. The label and/or the instructions can indicate directions for in vivo use of the pharmaceutical composition. The label and/or the instructions can indicate that the pharmaceutical composition may be used alone, or in combination with another agent to treat diseases or conditions described herein.

The label can indicate appropriate dosages for the agents of the invention as described supra. Suitable containers include, for example, a bottle. The containers can be formed from a variety of materials such as glass or plastic. The glass or plastic may be transparent, translucent or opaque. The glass or plastic may be amber. The glass or plastic may be covered with a light protecting material.

ADVANTAGES OF THE INVENTION

The invention disclosed herein relates to the surprising discovery that midodrine can be formulated in a solution or liquid form without the presence of alcohol and still maintain stability of the active agent. Further, the current invention provides an advantage by providing a new proprietary oral solution of midodrine hydrochloride for patients with underlying medical issues such as difficulty in swallowing oral tablets. In those cases, oral solution which offers ease of administration, convenience, and improved compliance can be highly beneficial and productive.

As discussed supra, current midodrine HCL liquid formulations includes about 14.6% alcohol (i.e., ethanol) by volume. This high percentage of alcohol makes such formulations undesirable for pediatric use or geriatric use. There is currently no commercially available stable midodrine HCL liquid formulations free of alcohol or substantially reduced alcohol to treat diseases described herein.

The following examples are presented to illustrate the present invention and to assist one of ordinary skill in making and using the same. The examples are not intended in any way to otherwise limit the scope of the invention.

EXAMPLES

Example 1

TABLE 1

Test Midodrine Oral Liquid Formulations.
Midodrine Hydrochloride Oral Solution

| Ingredients | Function | Formulation | | | | | | | | |
|---|---|---|---|---|---|---|---|---|---|---|
| | | I | II | III | IV | V | VI | VII | VIII | IX |
| | | Formulation Name | | | | | | | | |
| | | Sodium Benzoate | Maltitol 500 mg | Sodium Saccharine | Maltitol 125 mg | Xylitol | Sucralose | Aspartame | Sorbitol | Without Sucralose |
| | | Concentration (mg/mL) | | | | | | | | |
| Midodrine HCl | Active | 0.5 | 0.5 | 0.5 | 0.5 | 0.5 | 0.5 | 0.5 | 0.5 | 0.5 |
| Maltitol | Sweetener | 500 | 500 | — | 125 | — | — | — | — | — |
| Sodium Saccharine | Sweetener | — | — | 2 | — | — | — | — | — | — |
| Xylitol | Sweetener | — | — | — | — | 250 | — | — | — | — |
| Sucralose | Sweetener | — | — | — | — | — | 2 | — | — | — |
| Aspartame | Sweetener | — | — | — | — | — | — | 2 | — | — |
| Sorbitol Solution, 70% | Sweetener | — | — | — | — | — | — | — | 200 | — |
| Methylparaben | Preservative | — | 1.8 | 1.8 | 1.8 | 1.8 | 1.8 | 1.8 | 1.8 | 1.8 |
| Propylparaben | Preservative | — | 0.2 | 0.2 | 0.2 | 0.2 | 0.2 | 0.2 | 0.2 | 0.2 |
| Sodium Benzoate | Preservative | 1 | — | — | — | — | — | — | — | — |
| EDTA | Chelating agent | 0.5 | — | — | — | — | — | — | — | — |
| Orange Vanilla Flavor | Flavor | 1.5 | 1.5 | 1.5 | 1.5 | 1.5 | 1.5 | 1.5 | 1.5 | 1.5 |
| HCl/NaOH | pH adjustment Agent | Q.S to adjust pH | | | | | | | | |
| Purified Water | Carrier Vehicle | Q.S to 1 mL | | | | | | | | |

EDTA = Ethylenediaminetetraacetic acid;
"—" = Not used in formulation
** pH of the formulations were adjusted to pH 2.5, 3.5, 4.0, 5.0 or 8.0

Manufacturing Process for Midodrine HCL Formulations II to IX

Approximately 60% of required batch weight of purified water was charged into the batch tank. Mixing was initiated such that a vortex is generated. The purified water was heated in the batch tank to a temperature between 75° C.±5 ° C. The dispensed quantity of methylparaben was added slowly to the batch tank. The methylparaben beaker/container using purified water was thoroughly rinsed. Add the rinse to the batch tank. Mix for no longer than (NLT) 30 minutes or until dissolve. Maintain temperature 75° C.±5° C. during solubilization.

Add slowly the dispensed quantity of propylparaben to the batch tank. Thoroughly rinse the propylparaben beaker/container using purified water. Add the rinse to the batch tank. Mix for NLT 30 minutes or until dissolved. Maintain temperature 75° C.±5° C. during solubilization. Record RPM, temperature and appearance of the solution. While mixing enough to maintain a vortex, cool the solution in the batch tank to 50° C.±5° C.

Add slowly the dispensed quantity of Sweetener into the batch tank (except in the case of without sucralose formulation; also referred to as no sucralose formulation). Thoroughly rinse beaker/container used for weighing sweetener using purified water. Add the rinse to the batch tank. Mix for NLT 15 minutes or until dissolved. Maintain temperature 50° C.±5° C. during solubilization. While mixing enough to maintain a vortex, cool the solution in the batch tank to 20° C. to 30° C.

Add slowly the dispensed quantity of midodrine HCL to the batch tank. Thoroughly rinse the midodrine HCL beaker/container using purified water. Add the rinse to the batch tank. Mix for NLT 20 minutes or until dissolved.

Add slowly the dispensed quantity of Orange Vanilla Flavor to the batch tank. Thoroughly rinse the orange vanilla flavor beaker/container using purified water. Mix for NLT 15 minutes or until dissolved. Add the rinse to the batch tank.

Q.S. to 95% of the target batch size using purified water. Mix for NLT 10 min. Adjust the pH of the bulk solution to required pH (pH 2.5, 4.0, 5.0 or 8.0) using 0.1 N HCl/0.1 N NaOH. Q.S. to 100% of the target batch size using purified water.

Manufacturing Process for Formulation I

Charge approximately 60% of required batch weight of purified water into the batch tank. Initiate mixing such that a vortex is generated. Heat the purified water in the batch tank to a temperature between 50° C.±5 ° C. Add slowly the dispensed quantity of Sodium Benzoate to the batch tank. Thoroughly rinse the sodium benzoate beaker/container using purified water. Add the rinse to the batch tank. Mix for NLT 20 minutes or until dissolved. Maintain temperature 50° C.±5° C. during solubilization.

Add slowly the dispensed quantity of EDTA to the batch tank. Thoroughly rinse the EDTA beaker/container using purified water. Add the rinse to the batch tank. Mix for NLT 20 minutes or until dissolved. Maintain temperature 50° C.±5° C. during solubilization. Record RPM, temperature and appearance of the solution Add slowly the dispensed quantity of Sweetener into the batch tank. Thoroughly rinse beaker/container used for weighing sweetener using purified water. Add the rinse to the batch tank. Mix for NLT 15 minutes or until dissolved. Maintain temperature 50° C.±5° C. during solubilization. While mixing enough to maintain a vortex, cool the solution in the batch tank to 20° C. to 30° C.

Add slowly the dispensed quantity of midodrine HCL to the batch tank. Thoroughly rinse the midodrine HCL beaker/container using purified water. Add the rinse to the batch tank. Mix for NLT 20 minutes or until dissolved.

Add slowly the dispensed quantity of orange vanilla flavor to the batch tank. Thoroughly rinse the orange vanilla flavor beaker/container using purified water. Mix for NLT 15 minutes or until dissolved. Add the rinse to the batch tank. Record RPM, temperature and appearance of the solution. Q.S. to 95% of the target batch size using purified water. Mix for NLT 10 min. Adjust the pH of the bulk solution to required pH (pH 2.5, 4.0 or 8.0) using 0.1 N HCl/0.1 N NaOH. Q.S. to 100% of the target batch size using purified water.

Stability Study

Samples, 30 mL fill, from each batch were filled into amber PET bottles and were placed at super accelerated (50° C. at ambient humidity), accelerated (40° C.±2° C./75%±5% RH) and long-term (25° C.±2° C./60%±5% RH) storage conditions. Samples were withdrawn at pre-determined time points and analyzed for related compounds. All the samples were analyzed for related compounds using following method.

Related Compounds Method (HPLC) for Midodrine Hydrochloride Oral Solution

1. Mobile Phase and Diluent

Mobile Phase A: Buffer Solution (pH 4.0): Weigh and dissolve about 3.0 g of ammonium acetate in 1000 mL of water, add 1 mL triethylamine in it and adjust to pH 4.0±0.05 with diluted phosphoric acid, and filter through 0.45 μm nylon membrane disc filter.

Mobile Phase B: Acetonitrile

Diluent: Mix buffer solution and acetonitrile in the ratio of 95:05 v/v respectively, mix well and degassed by sonication 2. Chromatographic Conditions Column: YMC Pack ODS-A 4.6×250 mm 5 μm, Part # AA12S05-2546WT 3. Gradient Program

TABLE 2

| \multicolumn{4}{c}{Gradient HPLC Analysis Program for Midodrine Oral Solution.} |
| Time (min) | Flow rate (mL/min) | Mobile phase A (%) | Mobile phase B (%) |
| --- | --- | --- | --- |
| 0 | 1 | 95 | 5 |
| 5 | 1 | 95 | 5 |
| 40 | 1 | 60 | 40 |
| 50 | 1 | 60 | 40 |
| 51 | 1 | 95 | 5 |
| 60 | 1 | 95 | 5 |

4. Preparation of Blank: Use Diluent as Blank

5. Preparation of Midodrine Hydrochloride Standard Stock Solution

Weigh accurately about 50 mg of midodrine hydrochloride standard in 100 mL volumetric flask. Add 60 mL of diluent, sonicate to dissolve and dilute up to the mark with diluent. Further dilute 4 mL to 100 mL with diluent. (Concentration of midodrine hydrochloride standard stock solution: 20 ppm).

6. Preparation of Midodrine Related Compound A Stock Solution

Weigh accurately about 2.5 mg of midodrine related compound A (i.e., desglymidodrine) standard in 100 mL volumetric flask. Add 60 mL of diluent, sonicate to dissolve and dilute up to the mark with diluent. (Concentration of midodrine hydrochloride related compound A stock solution: 25 ppm).

7. Preparation of Standard Solution

Dilute 1 mL of Midodrine Hydrochloride standard stock solution and 2 mL of midodrine-related compound A solution dilute to 50 mL with diluent. (Concentration of midodrine hydrochloride standard solution: about 0.4 ppm). (Concentration of midodrine related compound A solution: about 1 ppm).

8. Preparation of Sample Solution

Transfer 4 mL of sample solution into 10 ml volumetric flask, add 5 mL of diluent, shake well for 5 minute and dilute up to the mark with diluent, mix well and filter through 0.45 μm PVDF syringe filter.

9. Preparation of Placebo Solution

Transfer 4 mL of placebo solution into 10 ml volumetric flask, add 5 mL of diluent, shake well for 5 minute and dilute up to the mark with diluent, mix well and filter through 0.45 μm PVDF syringe filter.

10. Calculations

Calculate the % impurity of midodrine related compound A in Midodrine Hydrochloride Oral Solution as given below:

$$\% \text{ Related Compound } A = \frac{AT1}{AS1} \times \frac{WS1}{100} \times \frac{2}{50} \times \frac{10}{4} \times \frac{P1}{100} \times \frac{100}{LC}$$

Where,

| | |
|---|---|
| AT1: | Peak area of midodrine-related compound A in the chromatogram of sample solution. |
| AS1: | Average peak area of midodrine-related compound A in the chromatogram of standard solution. |
| WS1: | Weight of midodrine-related compound A standard in mg. |
| P1: | % Potency of midodrine-related compound A standard on as is basis. |
| LC: | Label claim of midodrine hydrochloride in mg. |

An impurity may be a component that is not the drug substance (active pharmaceutical ingredient of the formulation, e.g., midodrine or midodrine salt, such as midodrine HCl) excluding water or an excipient in the formulation.

Calculate the % Individual unknown impurity present in Midodrine Hydrochloride Oral Solution as given below:

$$\% \text{ Individual Unknown Impurity} = \frac{AT2}{AS2} \times \frac{WS2}{100} \times \frac{4}{100} \times \frac{1}{50} \times \frac{10}{4} \times \frac{P2}{100} \times \frac{100}{LC}$$

Where,

| | |
|---|---|
| AT2: | Peak area of unknown impurity in the chromatogram of sample solution |
| AS2: | Average peak area of midodrine hydrochloride in the chromatogram of standard solution. |
| WS2: | Weight of midodrine hydrochloride standard in mg. |
| P2: | % Potency of midodrine hydrochloride standard on as is basis. |
| LC: | Label claim of midodrine hydrochloride in mg. |

Example 2

TABLE 3

Solubility of Midodrine Hydrochloride in Various Solvents and pH Values.

| Solvent | Solubility (mg/mL) |
|---|---|
| Water | >10 |
| 0.1N Hydrochloric Acid | >10 |
| 0.01N Hydrochloric Acid | >10 |
| Simulated Gastric Fluid (SGF) pH 1.25 | >10 |
| Potassium Phosphate Buffer, pH 2.5 | >10 |
| Potassium Phosphate Buffer, pH 3.5 | >10 |
| Potassium Phosphate Buffer, pH 4.5 | >10 |
| Potassium Phosphate Buffer, pH 5.5 | >10 |
| Potassium Phosphate Buffer, pH 6.0 | >10 |
| Potassium Phosphate Buffer, pH 6.8 | >10 |
| Potassium Phosphate Buffer, pH 7.2 | >10 |
| Potassium Phosphate Buffer, pH 7.5 | >10 |

TABLE 4

Percent Total Impurities for Formulations at 1 Month, 50° C. as a Function of pH.

| | 1 Month, 50° C., Total Impurities (%) | | | | | |
|---|---|---|---|---|---|---|
| Formulation pH | Maltitol 500 mg | Xylitol | Sucralose | Aspartame | Sorbitol | Without Sucralose |
| pH 2.5 | 2.0 | 2.3 | 1.8 | 2.1 | 2.3 | 1.6 |
| pH 4.0 | 5.6 | 5.7 | 3.6 | 3.5 | 5.2 | 4.1 |
| pH 5.0 | 13.8 | 10.1 | 3.6 | 4.2 | 7.5 | 3.8 |
| pH 8.0 | 23.7 | 17.4 | 7.3 | 5.3 | 11.6 | 11.5 |

TABLE 5

Percent Total Impurities for Formulations at 3 Months, 40° C. ± 2° C./75% ± 5% RH as a Function of pH.

| | 3 Month, 40° C., Total Impurities (%) | | | | | |
|---|---|---|---|---|---|---|
| Formulation pH | Maltitol 500 mg | Xylitol | Sucralose | Aspartame | Sorbitol | Without Sucralose |
| pH 2.5 | 2.4 | 1.4 | 1.9 | 1.8 | 3.7 | 1.5 |
| pH 4.0 | 5.4 | 4.7 | 3.2 | 3.0 | 4.6 | 3.8 |
| pH 5.0 | 15.0 | 9.8 | 3.1 | 3.4 | 7.9 | 3.6 |
| pH 8.0 | Not Tested | 26.1 | 6.5 | Not Tested | Not Tested | 15.8 |

TABLE 6

Percent Total Impurities for Formulations at 3 Months, 25° C. ± 2° C./60% ± 5% RH as a Function of pH.

| | 3 Months, 25° C., Total Impurities (%) | | | | | |
|---|---|---|---|---|---|---|
| Formulation pH | Maltitol 500 mg | Xylitol | Sucralose | Aspartame | Sorbitol | Without Sucralose |
| pH 2.5 | 0.5 | 0.4 | 0.4 | 0.7 | 0.8 | 0.3 |
| pH 4.0 | 0.7 | 0.7 | 0.5 | 0.6 | 0.7 | 0.9 |
| pH 5.0 | 3.6 | 2.0 | 0.5 | 0.6 | 1.7 | 0.8 |
| pH 8.0 | Not Tested | 11.3 | 3.0 | Not Tested | Not Tested | 3.7 |

TABLE 7

Effect of Sucralose on Total Impurities as a function of Formulation pH at Various Stability Condition.

| | Total Impurities (%) | | | | | | | | |
|---|---|---|---|---|---|---|---|---|---|
| | 1 month, 50° C. | | | 3 months, 40° C. ± 2° C./75% ± 5% RH | | | 3 months, 25° C. ± 2° C./60% ± 5% RH | | |
| pH | Sucralose | Without Sucralose | Difference | Sucralose | Without Sucralose | Difference | Sucralose | Without Sucralose | Difference |
| pH 2.5 | 1.8 | 1.6 | ↑ 0.2 | 1.9 | 1.5 | ↑ 0.4 | 0.4 | 0.3 | ↑ 0.1 |
| pH 4.0 | 3.6 | 4.1 | ↓ −0.5 | 3.2 | 3.8 | ↓ −0.6 | 0.5 | 0.9 | ↓ −0.4 |
| pH 5.0 | 3.6 | 3.8 | ↓ −0.2 | 3.1 | 3.6 | ↓ −0.5 | 0.5 | 0.8 | ↓ −0.3 |
| pH 8.0 | 7.3 | 11.5 | ↓ −4.2 | 6.5 | 15.8 | ↓ −9.3 | 3.0 | 3.7 | ↓ −0.7 |

TABLE 8

Percent Decrease or Inhibition of Midodrine Degradation at Different pH Values by Sucralose (compared to same formulation at the same pH but without sucralose).

| | % Decrease or Inhibition of Midodrine Degradation by Sucralose Compared to Same Formulation Without Sucralose | | |
|---|---|---|---|
| pH | 1 month, 50° C. | 3 months, 40° C. ± 2° C./75% ± 5% RH | 3 months, 25° C. ± 2° C./60% ± 5% RH |
| pH 4.0 | 12.2 | 15.8 | 44.4 |
| pH 5.0 | 5.3 | 13.9 | 37.5 |
| pH 8.0 | 36.5 | 58.9 | 18.9 |

TABLE 9

Stability Results for Midodrine Hydrochloride Oral Solution, 2.5 mg/5 mL, pH 3.5.

| Temp | Time Period | Assay of Midodrine HCl (% LC) | Total Impurities (%) |
|---|---|---|---|
| | Initial | 98.7 | 0.1 |
| 50° C. | 2 Weeks | 98.0 | 1.5 |
| | 1 Month | 97.3 | 2.9 |
| 40° C. ± 2° C./75% ± 5% RH | 1 Month | 97.9 | 1.0 |
| | 2 Months | 97.7 | 2.4 |
| | 3 Months | 97.4 | 2.8 |
| | 6 Months | 92.4 | 6.5 |
| 30° C. ± 2° C./65% ± 5% RH | 3 Months | 99.6 | 0.9 |
| | 6 Months | 95.6 | 1.8 |
| 25° C. ± 2° C./60% ± 5% RH | 3 Months | 99.2 | 0.4 |
| | 6 Months | 97.9 | 1.1 |

TABLE 10

Formulation Composition of Midodrine Hydrochloride Oral Solution, 2.5 mg/5 mL, pH 3.5 Lot Used in Table 9 (above).

| Ingredient | Quantity (mg/mL) |
|---|---|
| Midodrine HCl | 0.50 |
| Sucralose | 2.00 |
| Methylparaben | 1.80 |
| Propylparaben | 0.20 |
| HCl/NaOH | Q.S to adjust pH to 3.5 |
| Orange Vanilla Flavor | 1.50 |
| Purified Water | Q.S. to 1 mL |

TABLE 11

Total Impurities of Formulation With or Without Sucralose at pH 3.5.

| | | Total Impurities (%) | |
|---|---|---|---|
| Temp | Time Period | Sucralose | Without Sucralose |
| | Initial | 0.1 | 0.1 |
| 50° C. | 2 Weeks | 1.5 | 1.5 |
| | 1 Month | 2.9 | 3.5 |
| 40° C. ± 2° C./75% ± 5% RH | 1 Months | 1.0 | 1.0 |
| | 3 Months | 2.8 | 3.0 |
| 30° C. ± 2° C./65% ± 5% RH | 3 Months | 0.9 | 1.0 |
| 25° C. ± 2° C./60% ± 5% RH | 3 Months | 0.4 | 0.6 |

TABLE 12

Percent Decrease or Inhibition of Midodrine Degradation by Sucralose at pH 3.5 (compared to same formulation at pH 3.5 but without sucralose).

| Temp | Time Period | % Decrease or Inhibition of Midodrine Degradation by Sucralose |
|---|---|---|
| 50° C. | 1 Month | 17.1 |
| 40° C. ± 2° C./75% ± 5% RH | 3 Months | 6.7 |
| 30° C. ± 2° C./65% ± 5% RH | 3 Months | 10.0 |
| 25° C. + 2° C./60% ± 5% RH | 3 Months | 33.3 |

Example 3

TABLE 13

Exemplary Midodrine Oral Liquid Formulation.

| Ingredient | Quantity (mg/mL) |
| --- | --- |
| Midodrine HCl | 0.50 |
| Sucralose | 2.00 |
| Methylparaben | 1.80 |
| Propylparaben | 0.20 |
| HCl/NaOH | Q.S to adjust pH to 3.5 |
| Orange Vanilla Flavor | 1.50 |
| Purified Water | Q.S. to 1 mL |

TABLE 14

Alternative Midodrine Oral Liquid Formulations Stabilized by Sucralose.

| Ingredient | Quantity (mg/mL) |
| --- | --- |
| Midodrine HCl | 0.1-15 |
| Sucralose | 0.01-100 |
| Methylparaben | 1.1-2.5 |
| Propylparaben | 0.1-0.4 |
| HCl/NaOH | Q.S to adjust pH to 2.5-7.0 |
| Orange Vanilla Flavor | 0.75-2.25 |
| Purified Water | Q.S. to 1 mL |

REFERENCES

1. Parsaik A K, Singh B, Altayar O, Mascarenhas S S, Singh S S, Erwin P J and Murad H (2016), Midodrine for orthostatic hypotension: A systemic review and meta-analysis of clinical trials. J Gen Intern Med. 28(11):1496-1503.
2. Arnold A C and Shibao C (2013), Current concepts in orthostatic hypotension management. Curr Hypertens Rep. 15(4): 304-312.
3. Ricci F, De Caterina R, Fedorowski A (2015), Orthostatic Hypotension Epidemiology, Prognosis, and Treatment, J. American College of Cardiology, 66 (7), 848- 860.
4. Product Monograph, Midodrine hydrochloride Tablets 2.5 mg and 5 mg AAPharma Inc. Vaughan, Ontario, July 2010
5. Shire's package insert labeling for ProAmantine® (midodrine hydrochloride) Tablets from DailyMed website.
6. Mylan's package insert labeling for Midodrine Hydrochloride Tablet from DailyMed website.
7. Gulton (Midodrine Hydrochloride) 2.5 and 5 mg Tablet, Data Sheet (Douglas Pharmaceuticals), 3 Feb. 2015.
8. Smith W, Wan H, Much D, Robinson A G and Martin P (2016), Clinical benefit of midodrine hydrochloride in symptomatic orthostatic hypotension: a phase 4, double-blind, placebo-controlled, randomized, tilt-table study. Clin Auton Res, 26:267-277
9. Tilt-table study of the clinical efficacy of midodrine in symptomatic orthostatic hypotension (NCT01518946, n=24, completed June 20)
10. Clinical efficacy of midodrine in symptomatic orthostatic hypotension (NCT01515865, n=67, completed November 2013).
11. Midodrine Prevalence Report, Aug. 30, 2017

What is claimed is:

1. A stable, oral liquid formulation of midodrine comprising midodrine and sucralose, wherein the midodrine is midodrine HCl and wherein midodrine HCl and sucralose are present in the formulation in a midodrine HCl:sucralose ratio (w/w) of about 1:1 to about 1:10 wherein no more than about 10% by weight of a degradation product of midodrine is present after being stored for 1 month at 50 degrees Centigrade over a range of pH from 2.5 to 8.0.

2. A stable, oral liquid formulation of midodrine comprising midodrine and sucralose, wherein the midodrine is midodrine HCl and wherein midodrine HCl and sucralose are present in the formulation in a midodrine HCl:sucralose ratio (w/w) of about 1:1 to about 1:10 wherein no more than about 3.5% by weight of the degradation product of midodrine is present after being stored for 3 month at 25 degrees Centigrade over a range of pH from about 2.5 to 8.0.

3. The formulation of claim 1 or 2, wherein the ratio (w/w) of midodrine HCl to sucralose is about 1:4.

4. The formulation of claim 1 or 2, having a ratio of moles of midodrine to sucralose of less than 3:1.

5. The formulation of claim 1 or 2, having a ratio of moles of midodrine to sucralose of greater than 1:25.

6. The formulation of claim 1 or 2, having a ratio of moles of midodrine to sucralose of about 1:3.

7. The formulation of claim 1 or 2, wherein midodrine is midodrine HCl and wherein the formulation has about 0.5 mg/ml of midodrine HCl.

8. The formulation of claim 1 or 2, wherein midodrine is midodrine HCl and wherein the formulation has about $1.72 \times 10^{-3}$ M midodrine HCl.

9. The formulation of claim 1 or 2, wherein midodrine is midodrine HCl and wherein the formulation has about 0.5 mg/ml of midodrine HCl and 2 mg/ml sucralose.

10. The formulation of claim 1 or 2, wherein midodrine is midodrine HCl and wherein a ratio of moles of midodrine HCl to sucralose is greater than 1:4.

11. The formulation of claim 1 or 2, wherein a ratio of moles of midodrine to sucralose is less than 3:2.

12. The formulation of claim 1 or 2, wherein a ratio of moles of midodrine to sucralose is greater than 1:4 and less than 3:2.

13. The formulation of claim 1 or 2, wherein midodrine HCl is the only active agent or active pharmaceutical ingredient in the formulation.

14. The formulation of claim 1 or 2, wherein the formulation is essentially free of desglymidodrine added to the formulation, wherein any desglymidodrine in the formulation is formed by hydrolysis of midodrine in situ to desglymidodrine, and wherein hydrolysis of midodrine in situ to desglymidodrine is less than 10% of total midodrine used in the formulation.

15. The formulation of claim 2, wherein midodrine is midodrine HCl and wherein no more than about 3.0% by weight of the degradation product of midodrine HCl is present after being stored for 3 month at 25 degrees Centigrade at over a range of pH from about 3.5 to 8.0.

16. The formulation of claim 2, wherein midodrine is midodrine HCl and wherein no more than about 0.5% by weight of the degradation product of midodrine HCl is present after being stored for 3 month at 25 degrees Centigrade at over a range of pH from about 3.5 to 5.0.

* * * * *